United States Patent [19]

Shibahara et al.

[11] Patent Number: 4,534,898
[45] Date of Patent: Aug. 13, 1985

[54] 1-OXA-1-DETHIA-CEPHALOSPORIN DERIVATIVES

[75] Inventors: Seiji Shibahara, Machida; Tsuneo Okonogi, Yokohama; Yasushi Murai, Yokosuka; Shunzo Fukatsu, Tokyo; Tadashi Wakazawa; Taro Niida, both of Yokohama, all of Japan; Burton G. Christensen, Cliffside, N.J.

[73] Assignee: Merck & Co., Inc., Rahway, N.J.

[21] Appl. No.: 515,422

[22] Filed: Jul. 20, 1983

[30] Foreign Application Priority Data

Jul. 23, 1982 [JP] Japan ................................. 57-127574
Sep. 16, 1982 [JP] Japan ................................. 57-159548

[51] Int. Cl.$^3$ ............................................ C07D 419/14
[52] U.S. Cl. ................................... 260/245.3; 544/90; 544/92
[58] Field of Search ................. 260/245.3; 544/90, 92; 424/248.51, 248.54, 248.56

[56] References Cited

U.S. PATENT DOCUMENTS 4,226,886 10/1980 Christensen et al. .......... 424/248.51

FOREIGN PATENT DOCUMENTS 1592245 7/1981 United Kingdom ........... 424/248.54

Primary Examiner—Robert T. Bond
Attorney, Agent, or Firm—Thomas E. Arther; Raymond M. Speer; Hesna J. Pfeiffer

[57] ABSTRACT

This invention relates to 1-oxa-1-dethia-cephalosporins which are useful as anti-biotics.

4 Claims, No Drawings

1-OXA-1-DETHIA-CEPHALOSPORIN DERIVATIVES

BRIEF SUMMARY OF THE INVENTION

This invention relates to new 1-oxa-1-dethia-cephalosporins derivatives and pharmaceutically acceptable salts and esters thereof. More particularly, this invention concerns such 1-oxa-1-dethia-3-cephem derivatives and pharmaceutically acceptable salts or esters of the derivatives which are characterized by that 2-position of the cephem nucleus thereof is substituted by a lower alkyl group.

Advanced study has recently been made on the synthesis of various derivatives of 1-oxa-1-dethia-3-cephem compounds (see, for example, Japanese Patent Pre-publication "Kokai" No. 25551/78 and U.S. Pat. No. 4,226,866).

We have now succeeded in preparing 2-alkyl-substituted derivatives of 1-oxa-1-dethia-3-cephem compounds, and we have found that said new derivatives exhibit a higher antibacterial activity and a greater resistance to β-lactamase than those of the corresponding cephem compounds bearing no 2-alkyl substituent.

DETAILED DESCRIPTION OF THE INVENTION

According to this invention, there is provided a 2-alkyl-1-oxa-1-dethia-cephalosporin derivative of the general formula:

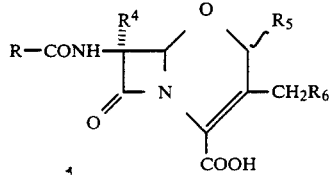

and a pharmaceutically acceptable salt or ester thereof, wherein R represents a group of the formula:

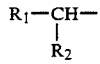

in which $R_1$ is a 2-thienyl or 3-thienyl group and $R_2$ is a hydrogen atom or a carboxyl group or R represents a group of the formula:

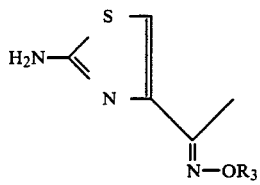

in which $R_3$ is a hydrogen atom, a lower alkyl or carboxyllower alkyl group; $R_4$ represents a hydrogen atom or a methoxy group, $R_5$ represents a lower alkyl group, particularly methyl group, $R_6$ represents hydrogen, azido, halo, cyano, quaternary ammonium, hydroxy, carbamoyloxy, N-loweralkyl carbamoyloxy, N,N-di-loweralkyl carbamoyloxy, amino, mercapto, loweralkylthio, loweralkanoyloxy, aroyloxy, or a 5- or 6-membered optionally substituted heterocyclic thio radical.

The preferred $R_6$ substituents are halo, hydroxy, pyridinium, carbamoyloxy, loweralkanoyloxy, and 5- or 6-membered heterocyclic. The optionally substituted 5- or 6-membered heterocyclic group contains from 1 to 4 heteroatoms selected from the group consisting of nitrogen, oxygen, sulfur; and may be, for example, tetrazol-5-ylthio; 1-methyltetrazol-5-ylthio; 1-carboxymethyltetrazol-5-ylthio; 1-sulfomethyltetrazol-5-ylthio; N,N-dimethylaminoethyltetrazol-5-ylthio; 1,3,4-thiadiazol-5-ylthio; 2-methyl-1,3,4-thiadiazol-5-ylthio; 2-carboxymethyl-3-methylthiazol-5-ylthio; 1,2,3-triazol-5-ylthio; 4-carboxy-3-hydroxy-1,2-oxazol-5-ylthio; 6-hydroxy-2-methyl-1,2,4-triazin-5-on-3-ylthio.

In accordance with the present invention, there is further provided a 7β-amino-2-alkyl-1-oxa-1-dethia-cephalosporin compound of the general formula:

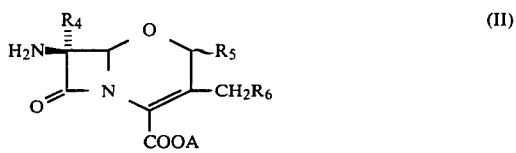

wherein $R_4$, $R_5$ and $R_6$ are as already defined above, and A represents a hydrogen atom or a carboxyl-protecting group. This compound is an intermediate useful in the synthesis of a 2-alkyl-1-oxa-1-dethia-cephalosporin derivative of Formula I which exhibits antibacterial activity, as described herein. Typical examples of the compound of Formula II include the following:

(1) 7β-Amino-7α-methoxy-2α-methyl-3-(1-methyl-1H-tetra-zole-5-yl)thiomethyl-1-oxa-1-dethia-3-cephem-4-carboxylic acid and its diphenylmethyl ester, (2) 7β-Amino-2α-methyl-3-(1-methyl-1H-tetrazole-5-yl)thiomethyl-1-oxa-1-dethia-3-cephem-4-carboxylic acid and its diphenylmethyl ester, (3) 7β-Amino-2β-methyl-3-(1-methyl-1H-tetrazole-5-yl)thiomethyl-1-oxa-1-dethia-3-cephem-4-carboxylic acid and its diphenylmethyl ester, (4) 7β-Amino-7α-methoxy-2β-methyl-3-(1-methyl-1H-tetrazole-5-yl)thiomethyl-1-oxa-1-dethia-3-cephem-4-carboxylic acid and its diphenylmethyl ester, (5) 7β-Amino-2β,3-dimethyl-1-oxa-1-dethia-3-cephem-4-carboxylic acid and its diphenylmethyl ester, and (6) 7β-Amino-2α,3-dimethyl-1-oxa-1-dethia-3-cephem-4-carboxylic acid and its diphenylmethyl ester.

In general Formulas (I) and (II), the lower alkyl means an alkyl group containing 1 to 4 carbon atoms. The lower alkyl group which $R_5$ represents may include the stereoconfigurations of α and β, and it is preferably methyl, either in α-configuration or in β-configuration. In the group $R_6$, the 5- or 6-membered optionally substituted heterocyclic radical may contain one to four heteroatoms selected from nitrogen, oxygen and sulfur and is preferably tetrazol-5-ylthio; 1-methyltetrazol-5-ylthio; 1-carboxymethyltetrazol-5-ylthio; 1-sulfomethyltetrazol-5-ylthio; N,N-dimethylaminoethyltetrazol-5-ylthio; 1,3,4-thiadiazol-5-ylthio; 2-methyl-1,3,4-thiadiazol-5-ylthio; 2-carboxymethyl-3-methyl-thiazol-5-ylthio; 1,2,3-triazol-5-ylthio; 4-carboxy-3-hydroxy-1,2-oxazol-5-ylthio; 6-hydroxy-2-methyl-1,2,4-triazin-5-on-3-ylthio. The substituent which may be present on the heterocyclic group includes a loweralkyl, alkoxy (1–6 carbon atoms), halo, cyano, carboxy, hydroxy, carbamoyl, N-substituted carbamoyl, azido, oxo, sulfo, amino, substituted amino, haloalkyl, carboxyalkyl, carbamoylalkyl, N-substituted carbamoylalkyl, guanidino, N-substituted guanidino, guanidinoalkyl, sulfamyl, substituted sulfamyl, loweralkyl substituted with any of the above substituents, and the like. Preferred substituents are methyl, carboxymethyl, sulfomethyl, dimethylaminoethyl, hydroxy, and oxo.

The pharmaceutically acceptable salt of a compound of the general formula (I) includes conventional nontoxic salts (carboxylates) which may be formed by the reaction with the carboxyl group present in said compound, especially such salts with an inorganic base, for example, alkali metal salts, for example sodium or potassium salt and alkaline earth metal salts such as calcium, magnesium or zinc salt; such addition salts with a basic amino acid, for example, lysine, arginine, ornithine or histidine; and such addition salts with an organic amine slat or other basic salts which will normally form a salt with cephalosporin.

Other nontoxic salts of the compound (I) include those which may be formed by addition to the amino group or another basic group of an inorganic acid such as hydrochloric, hydrobromic, sulfuric, nitric or phosphoric acid, an organic carboxylic or sulfonic acid such as trifluoroacetic, benzenesulfonic, methanesulfonic, maleic, tartaric or p-toluenesulfonic acid and an acidic amino acid such as aspartic or glutamic acid, and further they may include intermolecular or intramolecular salts.

The nontoxic esters of the compound (I) are those of the carboxyl group present in the latter with pharmaceutically acceptable ester-forming groups. Among these are preferred metabolically unstable esters, which carry an ester-forming group cleavable upon hydrolysis in vivo. Examples of the ester-forming group include aromatic groups such as acetoxymethyl, pivaloyloxymethyl, $\alpha$-ethoxycarbonyloxyethyl, phthalidyl and phenyl groups.

Typical examples of the compounds (I) according to this invention include the following:

| Compound No. | Compound Name |
|---|---|
| 1 | 7-(2-Thienylacetamido)-2$\alpha$-methyl-3-(1-methyl-1H—tetrazole-5-yl)thiomethyl-1-oxa-1-dethia-3-cephem-4-carboxylic acid |
| 2 | 7-(2-Thienylacetamido)-2$\beta$-methyl-3-(1-methyl-1H—tetrazole-5-yl)thiomethyl-1-oxa-1-dethia-3-cephem-4-carboxylic acid |
| 3 | 7$\beta$-(2-Thienylacetamido)-7$\alpha$-methoxy-2$\alpha$-methyl-3-(1-methyl-1H—tetrazole-5-yl)thiomethyl-1-oxa-1-dethia-3-cephem-4-carboxylic acid |
| 4 | 7$\beta$-(2-Thienylacetamido)-7$\alpha$-methoxy-2$\beta$-methyl-3-(1-methyl-1H—tetrazole-5-yl)thiomethyl-1-oxa-1-dethia-3-cephem-4-carboxylic acid |
| 5 | 7$\beta$-[2-(2-Thienyl)-2-carboxyacetamido]-7$\alpha$-methoxy-2$\alpha$-methyl-3-(1-methyl-1H—tetrazole-5-yl)thiomethyl-1-oxa-1-dethia-3-cephem-4-carboxylic acid |
| 6 | 7$\beta$-[2-(2-Thienyl)-2-carboxyacetamido]-7$\alpha$-methoxy-2$\beta$-methyl-3-(1-methyl-1H—tetrazole-5-yl)thiomethyl-1-oxa-1-dethia-3-cephem-4-carboxylic acid |
| 7 | 7$\beta$-[2-(3-Thienyl)-2-carboxyacetamido]-7$\alpha$-methoxy-2$\beta$-methyl-3-(1-methyl-1H—tetrazole-5-yl)thiomethyl-1-oxa-1-dethia-3-cephem-4-carboxylic acid |
| 8 | 7-[2-(2-Aminothiazole-4-yl)-2-methoxyiminoacetamido]-2$\alpha$-methyl-3-(1-methyl-1H—tetrazole-5-yl)thiomethyl-1-oxa-1-dethia-3-cephem-4-carboxylic acid |

The above-mentioned Compound Numbers are referred to in Table 1 given later.

The compounds (I) of this invention are clearly different from various cephem derivatives described in Japanese Patent Pre-publication ("Kokai") No. 25551/78 and U.S. Pat. No. 4,226,866 in respect of the presence of a lower alkyl group at 2-position of the cephem nucleus. Further, the compounds of the invention have a significantly improved antibacterial activity. Minimum inhibitory concentrations (M.I.C.) ($\mu$g/ml) of the compounds (I) to various bacteria are set out in Table 1 below. As will be seen from Table 1, the compounds of the invention are highly active against a variety of gram-positive and gram-negative bacteria, so that they act as useful antibiotics.

TABLE 1

| Test Microorganisms | MIC ($\mu$g/ml) of the compound of this invention | | | | | | |
|---|---|---|---|---|---|---|---|
| | Compound No. 1 | Compound No. 2 | Compound No. 3 | Compound No. 4 | Compound No. 5 | Compound No. 6 | Compound No. 7 |
| Staph. aureus Smith | 0.20 | 0.05 | 0.39 | 0.20 | 0.78 | 0.78 | 1.56 |
| Staph. aureus 209P JC-1 | 0.20 | 0.025 | 0.39 | 0.20 | 0.78 | 0.39 | 1.56 |
| E. Coli NIHJ JC-2 | 0.05 | 0.78 | 12.5 | 0.78 | 1.56 | 0.78 | 0.39 |
| Kl. pneumoniae PCI 602 | 0.10 | 1.56 | 25 | 1.56 | 1.56 | 1.56 | 0.05 |
| Pr. mirabilis GN79 | 0.10 | 12.5 | >100 | 12.5 | 0.78 | 0.10 | 0.20 |
| S. typhimurium LT-2 | 0.025 | 0.10 | 1.56 | 0.05 | 0.10 | ≦0.025 | ≦0.025 |
| Pr. vulgaris GN76 | 0.10 | 1.56 | 12.5 | 0.39 | 0.39 | 0.10 | 0.10 |
| Pr. rettgeri GN624 | 0.05 | 12.5 | >100 | 25 | 3.13 | ≦0.025 | 0.05 |
| C. freundii CN346 | 3.13 | 100 | >100 | 100 | 25 | 1.56 | 1.56 |
| Ent. cloacae G-0006 | 25 | 100 | >100 | 100 | 100 | 6.25 | 3.13 |
| Ser. marcescens No. 2 | 0.10 | 6.25 | 12.5 | 1.56 | 0.78 | 0.20 | 0.20 |
| Ps. aeruginosa | 12.5 | >100 | >100 | >100 | 100 | 25 | 25 |

As demonstrated in the above, the compounds of Formula (I) according to this invention exhibit excellent properties as the antibacterial agent, so that they are useful antibiotic which may be administered orally or parenterally for curative or preventative treatment of bacterial infections in mammalian animals, including man.

The compounds of Formula (I) and their pharmaceutically acceptable salts can be prepared by the following method:

The 7-amino group of a 2-alkyl-7-amino-1-oxa-1-dethia-cephem compound of the general formula:

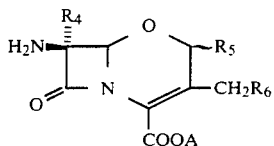
(II)

wherein $R_4$, $R_5$ and $R_6$ are as defined hereinabove and A represents a carboxyl-protecting group, for example, phenylmethyl or diphenylmethyl group, is condensed with a carboxylic acid of the formula:

R—COOH (Z)

wherein R is as defined hereinbefore or with a functional derivative of the carboxylic acid such as acid chloride or active ester, followed by removal of the protecting group (A).

The condensation (acylation) of the 7-amino group may be carried out by a known amidation procedure used for synthesis of ordinary β-lactam compounds. Thus, for example, the carbodiimide process is preferably used for direct condensation of the carboxylic acid (Z). With a functional derivative of the carboxylic acid (Z), the acylation may conveniently be performed according to the "acid halide" process, "active ester" process or "mixed acid anhydride" process.

The acylation is generally carried out in an organic solvent which will have no adverse effect on the reaction, for instance, methylene chloride, tetrahydrofuran, dioxane, ethyl acetate and the like. The reaction temperature has no limited range, although the reaction is normally effected under mild conditions, for example, under cooling or gentle heating.

The carboxyl-protecting group (A) for the 4-carboxyl group of the starting compound of the formula (II) includes any conventional ones which have been used in the art, for example, an aralkyl group or an alkyl group such as diphenylmethyl, p-nitrobenzyl and t-butyl groups. After completion of the acylation, the deprotection may be achieved by a known suitable method which depends on the nature of the protecting group employed, for example, by cleavage with an acid or reductive agent.

The carboxylic acid compounds of the formula (Z) to be used as starting material in the above method are known per se, but the cephem compounds of above formula (II) are novel, as not described in any literature. The general process for the preparation of the compounds (II) which we have developed is briefly stated below, and an Example is given hereinafter which illustrates the preparation of 2-methyl-7-amino-1-oxa-1-dethia-3-cephem-4-carboxylic acid as an example.

The compounds of Formula (II) according to this invention can be produced by a process essentially comprising the step of cyclizing an azetidinone derivative which is obtained by condensation of an oxazolin derivative with an α-hydroxyalkanoic acid alkyl ester. A process of producing the compound (II) starting from an azetidinone derivative of the formula (III) described hereinafter is schematically shown by the following reaction flow sheet:

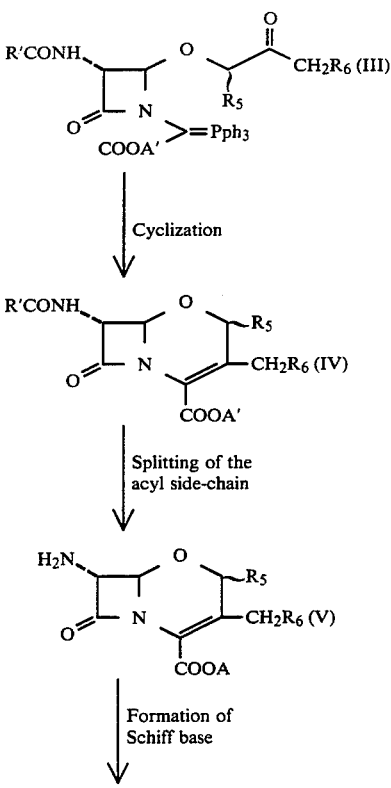

-continued

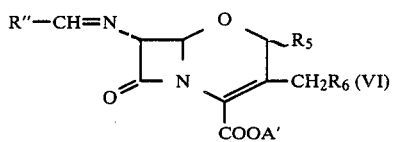

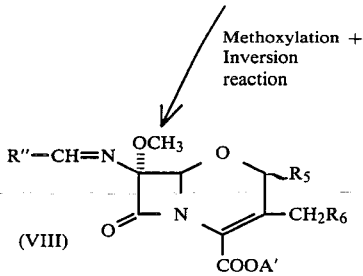

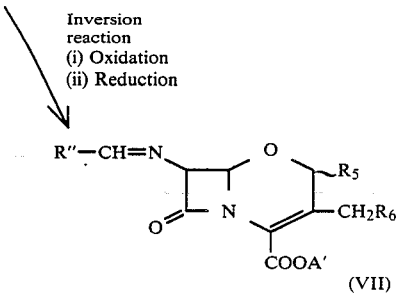

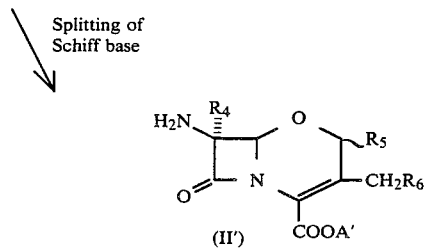

According to a further aspect of this invention, therefore, there is provided a process for the production of a 7β-amino-2-alkyl-1-oxa-1-dethia-cephalosporin compound of the general formula:

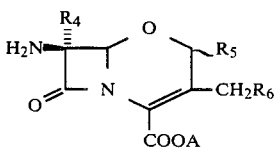

wherein $R_4$ represents a hydrogen atom or a methoxy group, $R_5$ represents a lower alkyl group, $R_6$ represents hydrogen, azido, halo, cyano, quaternary ammonium hydroxy, carbamoyloxy, N-loweralkyl carbamoyloxy, N,N-di-loweralkyl carbamoyloxy, amino, mercapto, loweralkylthio, loweralkanoyloxy, aroyloxy, or a 5- or 6-membered optionally substituted heterocyclic thio radical, and A represents a hydrogen atom or a carboxyl-protecting group, characterized in that the process comprises cyclizing an azetidinone compound of the formula:

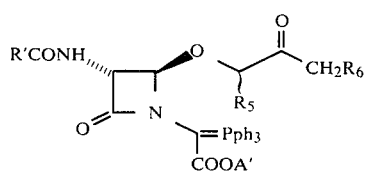

wherein the group R'CO— represents an acyl group, $R_5$ and $R_6$ are as defined above, ph represents a phenyl group and A' represents a carboxyl-protecting group, to produce a cephem compound of the formula:

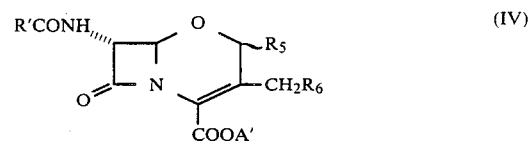

wherein R'CO—, $R_5$, $R_6$ and A' are as defined above; removing the group R'CO— from the 7α-amino group of the compound (IV) in a known manner to produce a compound of the formula:

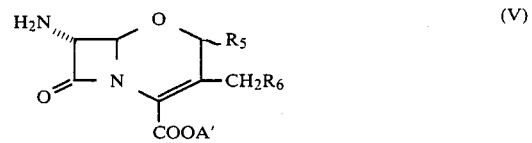

in which $R_5$, $R_6$ and A' are as defined above; reacting the compound (V) with an aromatic aldehyde to produce a compound in the form of a Schiff base-type compound of the formula:

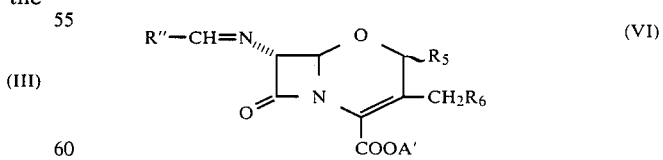

wherein $R_5$, $R_6$ and A' are as defined above and R" represents an aromatic group; subjecting the Schiff base-modified 7α-amino group of the compound (VI) to either a known reaction for steric inversion, or a known reaction for steric inversion accompanied by β-methoxylation at the 7-position of the compound (VI), thereby producing a compound of the formula:

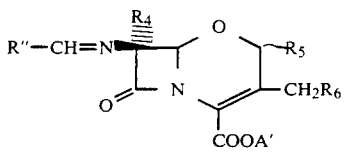

(VII')

wherein R4 represents a hydrogen atom or a methoxy group and R5, R6, R" and A' are as defined above; cleaving the Schiff base moiety R"—CH= from the compound (VII') in a conventional manner; and removing, if necessary, the carboxyl-protecting group (A') from the resultant product compound.

In the compound of the general Formulas (II) to (VIII) as concerned in the process of this invention, the groups R', R4, R5, R6 and A' all have the meanings defined above, and R" is an aromatic group, for example, an optionally substituted aryl group, especially phenyl group or 4-hydroxyphenyl group.

With the compound (II) of this invention and the starting compound (III) as used in the process of producing the compound (II), as well as the intermediate compounds (IV) to (VIII), the groups R', R4, R5, R6 and A' have the meanings as described below in detail. The acyl group as represented by the group R'CO— may generally be any aromatic acyl group. Thus, the group R' may be an aromatic group, for example, an aryl group, especially phenyl group or a substituted phenyl group, an arylalkyl group, an aryloxyalkyl group, an aralkyloxy group or a triphenylalkyl group. For instance, the group R'CO— may preferably be phenylcarbonyl, phenylacetyl, benzyloxycarbonyl, phenoxymethylcarbonyl or tritylcarbonyl group.

The lower alkyl group which R5 represents means an alkyl group containing 1 to 4 carbon atoms and may take a configuration of α or β. Either in α-configuration or in β-configuration, R5 is preferably a methyl group.

The halomethyl group which CH2R6 may represent includes a methyl group which has been substituted by one chlorine or bromine atom. In the group R6, the 5- or 6-membered optionally substituted heterocyclic radical may contain one to four heteroatoms selected from nitrogen, oxygen and sulfur and is preferably tetrazol-5-ylthio; 1-methyltetrazol-5-ylthio; 1-carboxymethyltetrazol-5-ylthio; 1-sulfomethyltetrazol-5-ylthio; N,N-dimethylaminoethyltetrazol-5-ylthio; 1,3,4-thiadiazol-5-ylthio; 2-methyl-1,3,4-thiadiazol-5-ylthio; 2-carboxymethyl-3-methyl-thiazol-5-ylthio; 1,2,3-triazol-5-ylthio; 4-carboxy-3-hydroxy-1,2-oxazol-5-ylthio; 6-hydroxy-2-methyl-1,2,4-triazin-5-on-3-ylthio. The substituent which may be present on the heterocyclic group includes a loweralkyl, alkoxy (1–6 carbon atoms), halo, cyano, carboxy, hydroxy, carbamoyl, N-substituted carbamoyl, azido, oxo, sulfo, amino, substituted amino, haloalkyl, carboxyalkyl, carbamoylalkyl, N-substituted carbamoylalkyl, guanidino, N-substituted guanidino, guanidinoalkyl, sulfamyl, substituted sulfamyl, loweralkyl substituted with any of the above substituents, and the like. Preferred substituents are methyl, carboxymethyl, sulfomethyl, dimethylaminoethyl, hydroxy, and oxo.

The group R" of the Schiff base residual group R"—CH= may generally be an aromatic group, especially an aryl, and it may preferably be a 4-hydroxyphenyl group. These aromatic groups may also be substituted for example, by a lower alkyl such as methyl, isopropyl or t-butyl. The position of the substitution by the lower alkyl group may preferably be 3,5-di-substitution.

The group A' may be a hydrogen atom or a carboxyl-protecting group. This carboxyl-protecting group may include any conventional ones which have been used for known cephalosporins and penicillins. For instance, A' may be a substituted or non-substituted aralkyl group such as diphenylmethyl, benzyl and p-nitrobenzyl, or a substituted or non-substituted alkyl group such as t-butyl and trichloroethyl.

The process of producing the compound of the general formula (II) according to this invention is now described in more detail with reference to the flow sheet of the process shown hereinbefore.

The cyclization reacting for converting the compound (III) into the compound (IV) is carried out first, and this reaction may be achieved by a process which comprises heating the compound (III) dissolved in an inert solvent, that is, by cyclizing the compound (III) according to the Wittig reaction. The reaction may be effected at a temperature of 40° to 120° C. and preferably of 100° to 120° C. The inert solvent available for this reaction includes THF, dioxane, benzene, toluene, xylene and ethers such as dimethoxyethane. The reaction is preferably carried out under an atmosphere of nitrogen or argon to prevent side-reactions from occurring and may be conducted in the presence of a catalytic amount of hydroquinone added as an antioxidant.

The group R5 in the compound (IV) takes the α-configuration when the group R5 in the compound (III) was of the R-configuration, or the group R5 takes the β-configuration when R5 in the compound (III) was of the S-configuration.

The two steps of producing the compound (V) from the compound (IV) and converting the compound (V) into the Schiff base type compound (VI) may be carried out each according to the conventional art. Thus, the former step of converting the compound (IV) into the compound (V) may be conducted by so-called iminohalide-iminoether method (see gazette of Japanese Patent Publication No. 13862/66). The latter step of converting the compound (V) into the compound (VI) for the formation of the Schiff base may be effected by reaction of the compound (V) with an aromatic aldehyde according to a method as described in the gazette of Japanese Patent Application Pre-publication "Kokai" No. 50394/75, and it can be achieved, for example, by condensing the compound (V) with an aromatic aldehyde such as 3,5-di-t-butyl-4-benzaldehyde in an inert solvent such as benzene, methylene chloride or ethyl acetate, with accompanying dehydration, to give the compound (VI).

The reaction for inversion by which the compound (VII) is produced from the compound (VI) may be accomplished by adding an oxidizing agent to a solution of the compound (VI) dissolved in an inert solvent, effecting the oxidation and removing the oxidizing agent, immediately followed by addition of a reducing agent. Thereby, the inversion of the steric configuration of the side-chain group at the 7-position will take place to give the compound (VII). The inert solvent used for this reaction may be any suitable one which has been employed for known reactions of β-lactam compounds, and it may preferably be chloroform or methylene chloride. Suitable examples of the oxidizing agent used include manganese dioxide, nickel peroxide, lead tetraacetate and dichlorodicyanobenzoquinone (DDQ).

Preferred examples of the reducing agent include sodium cyanoborohydride (NaBH₃CH), sodium borohydride (NaBH₄), tetraethylammonium borohydride (Et₄NBH₄) and tri-t-butoxy lithium aluminium hydride (Li(t-BuO)₃AlH). Both of these sequential reactions proceed at a temperature from −20° C. to 5° C.

The step of producing the compound (VIII) from the compound (VI) can be carried out by effecting the inversion reaction with accompanying methoxylation at the 7-position. For this purpose, a process as described in Japanese Patent Pre-publication "Kokai" No. 50394/75 may be conveniently employed.

The compounds (VII) and (VIII) so produced are then subjected to the reaction for decomposing (splitting) the Schiff base-type compound to give the desired intermediate compound (II). The reaction of decomposing (splitting) the Schiff base may be effected in a known manner, for example, by a hydrolysis method as disclosed in said publication "Kokai" No. 50394/75 or otherwise. If desired or required, the carboxyl-protecting group (A') may subsequently be removed from the compound (II) in a conventional manner.

The desired compounds (II) according to this invention are useful as intermediates since they can readily be converted into 7β-acyl-2-alkyl-1-oxa-1-dethia-cephalosporin compounds having a high anti-bacterial activity by a process comprising acylation of the 7-amino group and removal of the carboxyl-protecting group, as described further herein.

The compound (III) which is used as the starting material in the present invention is a new compound which is not described in any document, and hence a method for the preparation thereof is outlined below:

Thus the compound of the formula (III) can be prepared by multiple steps starting from, for example, a compound of the formula (IX):

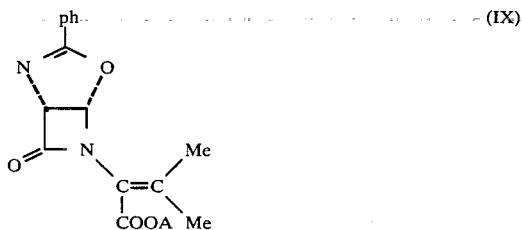

wherein Me represents a methyl group, A represents a hydrogen atom or a carboxyl-protecting group and ph represents a pheny group. An example of the compounds (IX) is benzhydryl 3-methyl-2-[(1R,5S)-3-phenyl-7-oxo-4-oxa-2,6-diazabicyclo(3,2,0)hepto-2-ene-6-yl]but-2-enoate which is disclosed in the "Journal of Chemical Society", Perkin I, page 1932 (1975).

The compound (IX) is reacted at ambient temperature in the presence of trichloromethanesulfonic acid with a DL-α-hydroxyalkanoic acid alkyl ester of the formula:

where R₅ is an alkyl group as mentioned for R₅ in Formula (I) and B is an alkyl group such as ethyl. There is thus obtained a diastereomer mixture comprising a (3R,4R)-4-[(1S)-1-alkoxycarbonylalkoxy]-3-benzamido-1-(1-protected carbonyl-2-methylprop-1-enyl)-azetidin-2-one having the structure:

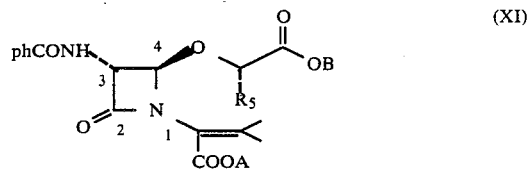

and a (3R,4R)-4-[(1R)-1-alkoxycarbonylalkoxy]-3-benzamido-1-(1-protected carbonyl-2-methylprop-1-enyl)-azetidin-2-one having the structure:

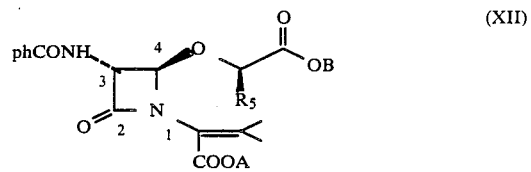

Said mixture can be chromtographed on silica gel using a developing solvent of benzene-ethyl acetate (7:1) so that the compounds of Formulas (XI) and (XII) are separated from each other.

If the compound (X) of the DL-form which is to be reacted with the compound (IX) is replaced by the corresponding compound of D-form (R-form) or L-form (S-form), the compound of the general formula (XI) or (XII) which is of the desired steric form can be obtained, respectively without effecting the subsequent, chromatographic separation (see Example 21 given hereinafter).

In order to form the desired cephem ring from the compound (XI) or (XII), there is carried out the subsequent step where the side-chain groups at the 1- and 4-positions of the azetidinone compound (XI) or (XII) are pretreated. The step for the pretreatment of the side-chain group at the 1-position of the compound (XI) or (XII) may be effected by such procedure as described below.

The compound of the formula (XII) is taken and oxidized by reacting with ozone gas in methylene chloride at a temperature below 0° C. to produce an oxidation product (which is unstable) of the formula:

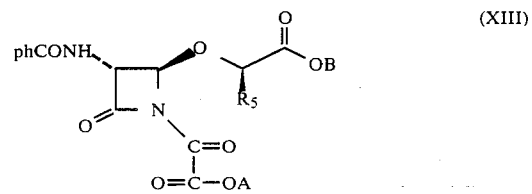

(By way of reference, a similar reaction has been described in a Reference Example of Japanese Patent Application No. 198466/81). The compound (XIII) is then reduced with zinc powder in acetic acid at a low temperature to produce an alcohol compound of the formula:

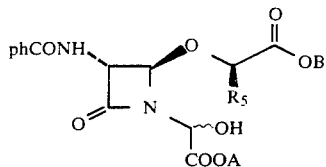
(XIV)

The alcohol (XIV) is chlorinated with thionyl chloride in methylene chloride in the presence of pyridine to give a chloro derivative of the formula:

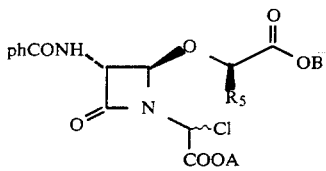
(XV)

The chloro compound of Formula (XV) is then treated with triphenyl phosphine in chloroform at room temperature in the presence of a tertiary amine such as a trialkylamine, whereby there takes place the reaction in which the chlorine atom of the compound (XV) is replaced by a triphenylphosphoranylidene group (phosphoranylidenation step), to produce a compound of the formula:

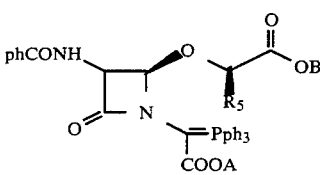
(XVI)

The pretreatment of the side-chain at the 1-position is thus completed, which is followed by a pretreatment of the other side-chain at the 4-position of the azetidinone compound. The compound (XVI) is hydrolyzed under alkaline conditions in the presence of sodium hydroxide or the like in aqueous acetone to remove the alkyl group (B). There is thus obtained a corresponding carboxylic acid compound (corresponding to such compound of the formula (XVI) where —OB has been converted into —OH). This carboxylic acid compound is treated for activation of the carboxyl group before it is subjected to the subsequent reactions. For this purpose, said carboxylic acid compound is interacted with ethyl chloroformate of the formula:

Cl—COOEt (XVII)

to effect the ethoxycarbonylation. This results in formation of a compound having the formula:

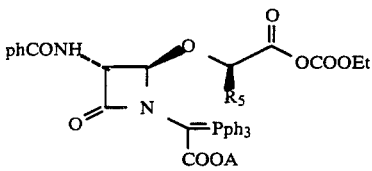
(XVIII)

The compound (XVIII) is reacted with diazomethane, in ethyl ether at a low temperature to effect the diazomethylation reaction, giving a diazo compound of the formula:

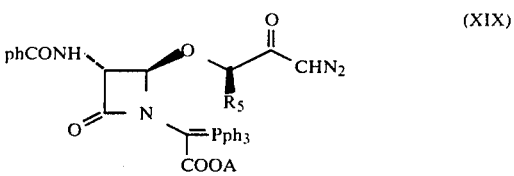
(XIX)

This diazo compound is then reacted with hydrogen chloride in dioxane, so that the diazo group is replaced by the chloro group, affording a chloro compound of the formula:

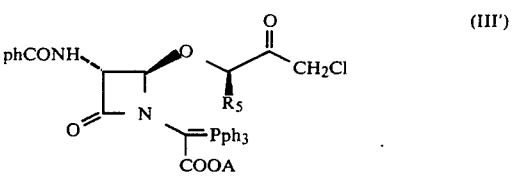
(III')

The chloro compound (III') is reacted with a heterocyclic thiol compound of the formula:

HS—Het (XX)

where —Het stands for a heterocyclic group as defined above for the substituent $R_6$, in methylene chloride in the presence of pyridine. There is so obtained a compound of the formula:

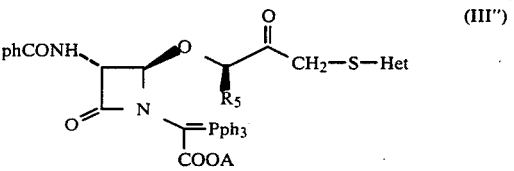
(III")

This compound (III") is heated in the presence of hydroquinone in toluene under heating to cause the cyclization, thereby producing a compound of the formula:

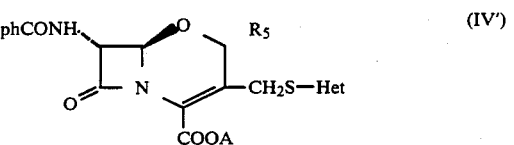
(IV')

which is a 7α-benzamido-2-alkyl-3-(heterocyclic)thioalkyl-1-oxa-1-dethia-3-cephem-4-carboxylic acid ester.

The foregoing descriptions are to explain the process starting from the compound of Formula (XII) where $R_5$ takes the R-configuration, but the same treatments as above can be applied to the compound of Formula (XI) where $R_5$ takes the S-configuration. When the product of such treatments is then subjected to the cyclization, there is formed the cephem ring. The alkyl group at the 2-position of the cephem ring as formed is of the α-configuration in the former case but is of the β-configuration in the latter case.

The above treatment of the compounds (XI) and (XII) may be carried out firstly in respect of the side-chain group at the 1-position and subsequently in respect of the side-chain group at the 4-position, or vice versa. In any case, the respective reactions can be effected under the same conditions as those stated above for the former case. Example 19 below illustrates the process where the side-chain at the 4-position was treated at first.

The compound of Formula (II) according to this invention where CH₂R₆ is a halomethyl group can be prepared also when for example, the compound of the general formula (III') is treated under the aforesaid cyclization conditions. However, the compound so obtained of the formula (IV) in which CH₂R₆ is a halomethyl group is unstable, so that it is preferred to convert firstly the compounds (III') into the compound (III'') as already stated, and subsequently to cyclize the latter. Example 20 illustrates the process of preparing the starting compound containing hydrogen as $R_6$, namely the compound of the formula (III) where CH₂R₆ is methyl, when the conversion of the 4-position takes place first. The process of Example 20 is characterized by the reduction of the compound of the general formula (III) where CH₂R₆ is a halomethyl group. The halogen in the halomethyl group to be reduced is most preferably iodine.

The reduction of the halomethyl group can likewise be conducted under the same reductive conditions as above in any event where said pretreatment of the side-chain group at the 1-position is preceded or followed by the pretreatment of the side-chain group at the 4-position.

Removal of the benzoyl group (phCO—) from the 7α-benzamido group of the compound (IV') may be effected by a known technique, for example, by reaction with phosphorus pentachloride in methylene chloride followed by treatment with methanol, as described in Japanese Patent Publication No. 13862/66. The result is formation of a compound of the formula:

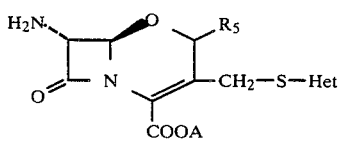

To invert the stereoconfiguration of the 7-amino group of the compound (II'') from α-type to β-type, a process, for example, as described in Japanese Patent Pre-publication ("Kokai") No. 50394/75 may be employed, the process comprising reacting the compound (II'') with 3,5-di-t-butyl-4-hydroxybenzaldehyde to give a corresponding compound in the form of Schiff base, followed by treatment with an oxidizing agent and reduction of the oxidized compound into the desired 7β-amino compound. For introduction of 7α-methoxy group into 7-position of the compound (II''), such a technique may be applied, for instance, as disclosed in Japanese Patent Pre-publication No. 50394/70.

Typical examples of the compounds represented by the general formula (II''') are shown below:

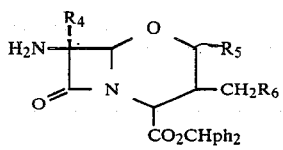

| $R_4$ | $R_5$ | CH₂R₆ | IR(CHCl₃) (cm⁻¹) |
|---|---|---|---|
| —OMe | α-Me | —CH₂—STz | 1782 1720 1603 |
| H | α-Me | " | 1785 1720 1602 |
| —OMe | β-Me | " | 1783 1720 1600 |
| H | β-Me | " | 1783 1720 1602 |

In above Table, —CH₂—STz stands for (1-methyl-1H-tetrazole-5-yl)thiomethyl group and Me stands for methyl group.

In a manner similar to that described above, compounds of the present invention of Formula (I) may be prepared, wherein $R_6$ is other than 5- or 6-membered optionally substituted heterocyclic thio, by reacting the compound of Formula (III'):

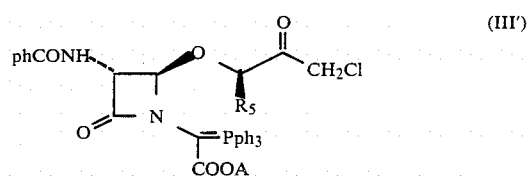

with a compound of the formula:

where $M^+R_6^{1-}$ is a salt, and $R_6^a$ is hydroxy, cyano, azido, whereby through base displacement followed by ring closure as described herein, the compound of the following formula is produced:

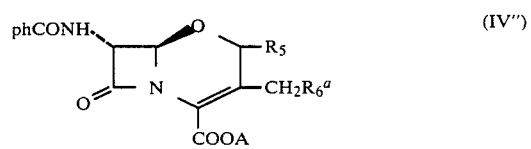

Compounds of Formula (IV''') may be further reacted in a known manner to afford other compounds of Formula (I) with additional $R_6$ substituents. For example, the azido group may be reduced to form the amino group, and acylation may be carried out to afford the lower alkanoyloxy group.

The following Examples illustrate the production of the compounds of this invention and preparation of the starting compounds, but these Examples in no way limit the invention.

EXAMPLE 1

(1) Production of diphenylmethyl 7-(2-thienylacetamido)-2α-methyl-3-(1-methyl-1H-tetrazole-5-yl)thiomethyl-1-oxa-1-dethia-3-cephem-4-carboxylate of the formula:

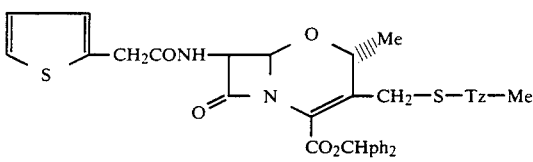

in which Me is methyl, Tz-Me is 1-methyl-1H-tetrazole-5-yl and ph is phenyl

Pyridine (27 mg) and then 0.5 ml of methylene chloride containing 50 mg of 2-thienylacetic acid chloride were added under ice-cooling to 4 ml of methylene chloride containing 128 mg of diphenylmethyl 7-amino-2α-methyl-3-(1-methyl-1H-tetrazole-5-yl)thiomethyl-1-oxa-1-dethia-3-cephem-4-carboxylate. The mixture was agitated at the same temperature for 30 minutes, and the resultant reaction solution was poured into 5 ml of ice water.

The organic layer was separated off, washed with saturated aqueous sodium bicarbonate and then with water, dried over MgSO$_4$ and evaporated under reduced pressure. The residue was purified by column chromatography on silica gel developed with a development solvent of benzene-ethyl acetate (5:1) to give 125 mg (78%) of the title compound, that is, diphenylmethyl 7-(2-thienylacetamido)-2α-methyl-3-(1-methyl-1H-tetrazole-5-yl)thiomethyl-1-oxa-1-dethia-3-cephem-4-carboxylate.

(2) Production of 7-(2-thienylacetamido)-2α-methyl-3-(1-methyl-1H-tetrazole-5-yl)thiomethyl-1-oxa-1-dethia-3-cephem-4-carboxylic acid of the formula:

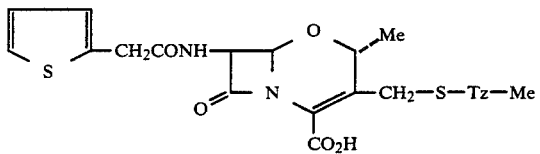

The product (100 mg) from step (1) above was added to the ice-cooled mixture of 0.1 ml of anisole and 1 ml of trifluoroacetic acid, followed by agitation at the same temperature for 30 minutes to effect the removal of the diphenylmethyl group (for the deprotection). The reaction solution so obtained was evaporated and the residue was pulverized by trituration with isopropyl ether to give 68 mg (93%) of the title compound.

IR (Nujol), $\nu_{max}$ (cm$^{-1}$): 1785, 1720, NMR (acetone-d$_6$), $\delta_{ppm}$: 1.58 (3H, d, j=6.8 Hz, 2-CH$_3$), 3.88 (2H, s, —CH$_2$CO—), 3.99 (3H, s, tetrazole 1-CH$_3$), 4.17 and 4.55 (each 1H, ABq, J=13.6 Hz, —CH$_2$S—), 4.97 (1H, q, J=6.8 Hz, 2-H), 5.38 (1H, d, J=4 Hz, 6-H), 5.68 (1H, dd, J=10, 4 Hz, 7-H), 6.80–7.35 (3H, m, thiophene).

EXAMPLE 2

(1) Production of diphenylmethyl 7-(2-thienylacetamido)-2β-methyl-3-(1-methyl-1H-tetrazole-5-yl)thiomethyl-1-oxa-1-dethia-3-cephem-4-carboxylate of the formula:

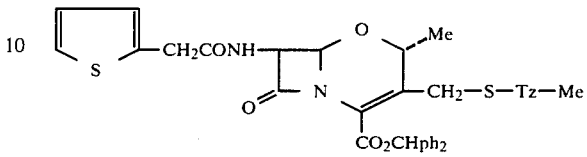

Pyridine (17 mg) and then 0.5 ml of methylene chloride containing 31 mg of 2-thienylacetic acid chloride were added under ice-cooling to 3 ml of methylene chloride containing 81 mg of diphenylmethyl 7-amino-2β-methyl-3-(1-methyl-1H-tetrazole-5-yl)thiomethyl-1-oxa-1-dethia-3-cephem-4-carboxylate. The mixture was agitated at the same temperature for 30 minutes and the resultant reaction solution was poured into 5 ml of ice water. The organic layer was separated off, washed with saturated aqueous sodium bicarbonate and then with water, dried over MgSO$_4$ and evaporated under reduced pressure. The residue was purified by column chromatography on silica gel developed with a development solvent of benzene-ethyl acetate (5:1) to give 82 mg (81%) of the title compound.

(2) Production of 7-(2-thienylacetamide)-2β-methyl-3-(1-methyl-1H-tetrazole-5-yl)thiomethyl-1-oxa-1-dethia-3-cephem-4-carboxylic acid:

97 mg of the product obtained in step (1) above was subjected to the deprotection reaction for removal of the diphenylmethyl group and then processed in the same manner as in Example 1-(2) to afford 64 mg (91%) of the title compound.

IR (Nujol), $\nu_{max}$ (cm$^{-1}$): 1782, 1720, NMR (acetone-d$_6$), $\delta_{ppm}$: 1.48 (3H, d, J=6.8 Hz, 2-CH$_3$), 3.85 (2H, s, —CH$_2$CO—), 3.98 (3H, s, tetrazole 1-CH$_3$), 4.10 and 4.87 (each 1H, ABq, J=13.0 Hz, —CH$_2$S—), 4.84 (1H, q, J=6.8 Hz, 2-H), 5.15 (1H, d, J=4.0, 6-H), 5.63 (1H, dd, J=9.3, 3.9 Hz, 7-H), 6.85–7.35 (3H, m, thiophene).

EXAMPLE 3

(1) Production of diphenylmethyl 7β-(2-thienylacetamido)-7α-methoxy-2α-methyl-3-(1-methyl-1H-tetrazole-5-yl)thiomethyl-1-oxa-1-dethia-3-cephem-4-carboxylate of the formula:

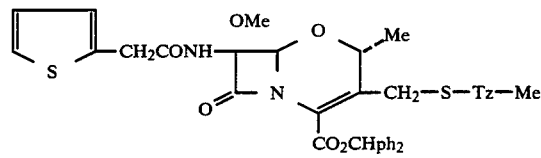

18 μl of pyridine and then 0.5 ml of methylene chloride containing 36 mg of 2-thienylacetic acid chloride were added under ice-cooling to 6 ml of methylene chloride containing 100 mg of diphenylmethyl 7β-amino-7α-methoxy-2α-methyl-3-(1-methyl-1H-tetrazole-5-yl)thiomethyl-1-oxa-1-dethia-3-cephem-4-carboxylate. The mixture was stirred at that temperature for 30 minutes and the resultant reaction solution was poured into 5 ml of ice water. The organic layer was separated off, washed with saturated aqueous sodium bicarbonate and then with water, dried over MgSO4 and evaporated under reduced pressure. The residue was purified by column chromatography on silica gel developed with a solvent of benzene-ethyl acetate (5:1) to give 101 mg (82%) of the title compound.

(2) Production of
7β-(2-thienylacetamide)-7α-methoxy-2α-methyl-3-(1-methyl-1H-tetrazole-5-yl)thiomethyl-1-oxa-1-dethia-3-cephem-4-carboxylic acid The product (120 mg) from step (1) above was added to the ice-cooled mixture of 0.2 ml of anisole and 2 ml of trifluoroacetic acid, followed by agitation at that temperature for 30 minutes to effect the deprotection reaction. The reaction solution so obtained was evaporated and the residue was triturated with isopropyl ether to give 76 mg (85%) of the title compound.

IR (Nujol), $v_{max}$ (cm$^{-1}$): 1780, 1710, NMR (acetone-d6), $\delta_{ppm}$: 1.57 (3H, d, J=6.7 Hz, 2-H), 3.44 (3H, s, —OCH3), 3.85 (2H, s, —CH2CO—), 3.97 (3H, s, tetrazole 1-CH3), 4.16 and 4.50 (each 1H, ABq, J=14 Hz, —CH2S—), 4.81 (1H, q, J=6.7 Hz, 2-H), 5.20 (1H, s, 6-H), 6.80–7.35 (3H, m, thiophene).

EXAMPLE 4

(1) Production of diphenylmethyl
7β-(2-thienylacetamido)-7α-methoxy-2β-methyl-3-(1-methyl-1H-tetrazole-5-yl)thiomethyl-1-oxa-1-dethia-3-cephem-4-carboxylate 12 μl of pyridine and then 0.5 ml of methylene chloride containing 22 mg of 2-thienylacetic acid chloride were added under ice-cooling to 3 ml of methylene chloride containing 65 mg of diphenylmethyl 7β-amino-7α-methoxy-2β-methyl-3-(1-methyl-1H-tetrazole-5-yl)thiomethyl-1-oxa-1-dethia-3-cephem-4-carboxylate. The mixture was agitated at that temperature for 30 minutes and the resultant reaction solution was poured into 5 ml of ice water.

The organic layer was separated off, washed with saturated aqueous sodium bicarbonate and then with water, dried over MgSO4 and evaporated under reduced pressure. The residue was purified by column chromatography on silica gel developed with a solvent of benzene-ethyl acetate (3:1) to give 70 mg (87%) of the title compound.

(2) Production of
7β-(2-thienylacetamido)-7α-methoxy-2β-methyl-3-(1-methyl-1H-tetrazole-5-yl)thiomethyl-1-oxa-1-dethia-3-cephem-4-carboxylic acid The product (115 mg) from step (1) above was subjected to the deprotection reaction, followed by after-treatment in the same manner as in Example 3(2) to give 75 mg (87%) of the title compound.

IR (Nujol), $v_{max}$ (cm$^{-1}$): 1782, 1712, NMR (acetone-d6), $\delta_{ppm}$: 1.38 (3H, d, J=6.9 Hz, 2-CH3), 3.46 (3H, s, —OCH3), 3.87 (2H, s, —CH2CO—), 3.98 (3H, s, tetrazole 1-CH3), 4.07 and 4.84 (each 1H, ABq, J=14 Hz, —CH2S—), 4.84 (1H, q, J=6.9 Hz, 2-H), 5.00 (1H, s, 6-H), 6.85–7.40 (3H, m, thiophene).

EXAMPLE 5

(1) Production of diphenylmethyl
7β-[2-(2-thienyl)-2-diphenylmethoxycarbonylacetamido]-7α-methoxy-2α-methyl-3-(1-methyl-1H-tetrazole-5-yl)thiomethyl-1-oxa-1-dethia-3-cephem-4-carboxylate of the formula:

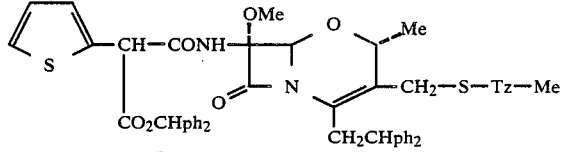

Monodiphenylmethyl 2-thienylmalonate (67 mg) and 100 mg of diphenylmethyl 7β-amino-7α-methoxy-2α-methyl-3-(1-methyl-1H-tetrazole-5-yl)thiomethyl-1-oxa-1-dethia-3-cephem-4-carboxylate were dissolved in 4 ml of methylene chloride, and the solution was cooled to −30° C. and then admixed with 61 μl of pyridine and 19 μl of phosphorus oxychloride. The admixture was agitated at a temperature of −30° to −10° C. for 30 minutes and then at −10° to 0° C. for further 30 minutes. The resultant reaction solution was poured into 5 ml of ice water and the organic layer was separated off, washed with saturated aqueous sodium bicarbonate and then with water and dried over MgSO4. The solvent was removed by evaporation under reduced pressure and the residue was purified by chromatography on a column of silica gel using a developing solvent of benzene-ethyl acetate (5:1) to give 117 mg (71%) of the title compound.

(2) Production of
7β-[2-(2-thienyl)-2-carboxyacetamido]-7α-methoxy-2α-methyl-3-(1-methyl-1H-tetrazole-5-yl)thiomethyl-1-oxa-1-dethia-3-cephem-4-carboxylic acid The product (117 mg) from step (1) above was subjected to the deprotection reaction and after-treatment by the same procedure as in Example 3-(2) to yield 59 mg (83%) of the title compound.

IR (Nujol), $v_{max}$ (cm$^{-1}$): 1782, 1722, NMR (acetone-d6), $\delta_{ppm}$: 1.53 (3H, d, 2-CH3), 3.42, 3.50 (3H, s, —OCH3), 3.96, 3.98 (3H, s, tetrazole 1-CH3), 4.17 and 4.51 (each 1H, ABq, —CH2S—), 4.80 (1H, q, 2-H), 5.16 (1H, s, 6-H), 5.23 (1H, s, —CH—CO—), 6.80–7.40 (3H, m, thiophene).

EXAMPLE 6

(1) Production of diphenylmethyl
7β-[2-(2-thienyl)-2-diphenylmethoxycarbonylacetamido]-7α-methoxy-2β-methyl-3-(1-methyl-1H-tetrazole-5-yl)thiomethyl-1-oxa-1-dethia-3-cephem-4-carboxylate Monodiphenylmethyl 2-thienylmalonate (40 mg) and 100 mg of diphenylmethyl 7β-amino-7α-methoxy-2β-methyl-3-(1-methyl-1H-tetrazole-5-yl)thiomethyl-1-oxa-1-dethia-3-cephem-4-carboxylate were dissolved in 3 ml of methylene chloride and the solution was cooled to −30° C. and then admixed with 37 μl of pyridine and 19 μl of phosphorus oxychloride. The admixture was agitated at a temperature of −30° to −10° C. for 30 minutes and then at −10° to 0° C. for further 30 minutes. The resultant reaction solution was poured into 5 ml of ice water and the organic layer was separated off, washed with saturated aqueous sodium bicarbonate and then with water and dried over MgSO₄. The solvent was removed by evaporation under reduced pressure, and the residue was purified by chromatography on a column of silica gel using a developing solvent of benzene-ethyl acetate (4:1) to give 80 mg (82%) of the title compound.

(2) Production of
7β-[2-(2-thienyl)-2-carboxyacetamido]-7α-methoxy-2β-methyl-3-(1-methyl-1H-tetrazole-5-yl)thiomethyl-1-oxa-1-dethia-3-cephem-4-carboxylic acid 160 mg of the product from step (1) above was subjected to the deprotection reaction and after-treatment by the same procedure as in Example 3-(2) to yield 79 mg (81%) of the title compound.

IR (Nujol), $\nu_{max}$ (cm⁻¹): 1780, 1715, NMR (acetone-d₆), $\delta_{ppm}$: 1.28, 1.39 (3H, d, 2-CH₃), 3.41, 3.49 (3H, s, —OCH₃), 3.98, 3.99 (3H, s, tetrazole 1-CH₃), 4.07, 4.82 (2H, ABq, —CH₂S—), 4.83 (1H, q, 2-H), 5.02 (1H, s, 6-H), 5.14, 5.16 (1H, s, —CH—CO—), 6.80–7.40 (3H, m, thiophene).

EXAMPLE 7

(1) Production of diphenylmethyl
7β-[2-(3-thienyl)-2-diphenylmethoxycarbonylacetamido]-7α-methoxy-2β-methyl-3-(1-methyl-1H-tetrazole-5-yl)thiomethyl-1-oxa-1-dethia-3-cephem-4-carboxylate of the formula:

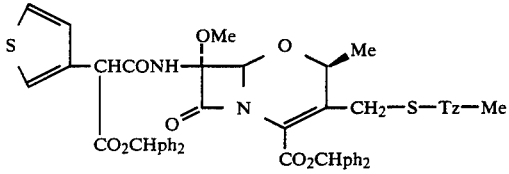

72 mg of monodiphenylmethyl 3-thienylmalonate and 90 mg of diphenylmethyl 7β-amino-7α-methoxy-2β-methyl-3-(1-methyl-1H-tetrazole-5-yl)thiomethyl-1-oxa-1-dethia-3-cephem-4-carboxylate were dissolved in 4 ml of methylene chloride, and the solution was cooled to −30° C. and then admixed with 55 μl of pyridine and 22 μl of phosphorus oxychloride. The admixture was agitated at a temperature of −30° to −10° C. for 30 minutes and then at −10° to 0° C. for further 30 minutes. The resultant reaction solution was poured into 5 ml of ice water and the organic layer was separated off, washed with saturated aqueous sodium bicarbonate and then with water and dried over MgSO₄. The solvent was removed by evaporation under reduced pressure and the residue was purified by chromatography on a column of silica gel using a developing solvent of benzene-ethyl acetate (5:1) to give 120 mg (82%) of the title compound.

(2) Production of
7β-[2-(3-thienyl)-2-carboxyacetamido]-7α-methoxy-2β-methyl-3-(1-methyl-1H-tetrazole-5-yl)thiomethyl-1-oxa-1-dethia-3-cephem-4-carboxylic acid 147 mg of the product from step (1) above was subjected to the deprotection reaction and after-treatment by the same procedure as in Example 3-(2) to yield 74 mg (83%) of the title compound.

IR (Nujol), $\nu_{max}$ (cm⁻¹): 1780, 1722, NMR (acetone-d₆), $\delta_{ppm}$: 1.32, 1.38 (3H, d, 2-CH₃), 3.39 3.46 (3H, s, —OCH₃), 3.98 (3H, s, tetrazole 1-CH₃), 4.06, 4.80 (2H, ABq, —CH₂S—), 4.83 (1H, q, 2-H), 4.92, 4.95 (1H, s, 6-H), 5.00, 5.02 (1H, s,

7.15–7.50 (3H, m, thiophene).

EXAMPLE 8

(1) Production of diphenylmethyl
7-[2-(2-tritylaminothiazole-4-yl)-2-methoxyiminoacetamido]-2α-methyl-3-(1-methyl-1H-tetrazole-5-yl)thiomethyl-1-oxa-1-dethia-3-cephem-4-carboxylate (syn-isomer) of the formula:

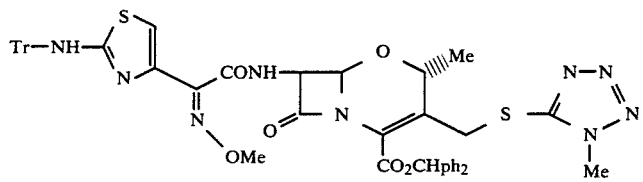

in which Tr stands for trityl group.

100 mg of diphenylmethyl 7-amino-2α-methyl-3-(1-methyl-1H-tetrazole-5-yl)thiomethyl-1-oxa-1-dethia-3-cephem-4-carboxylate and 99 mg of 2-(2-tritylaminothiazole-4-yl)-2-methoxyiminoacetic acid (syn-isomer) were dissolved in 3 ml of methylene chloride, and to the solution after cooling to −30° C. were added 65 μl of pyridine and 26 μl of phosphorus oxychloride. The mixture was stirred at a temperature of −30° to 0° C. for 30 minutes, and the reaction solution thus obtained was poured into 5 ml of ice water.

The organic layer was separated off, washed with saturated aqueous sodium bicarbonate and then with water before drying, and after drying the solvent was distilled off. The residue was purified by chromatography on a column of silica gel to give 156 mg (84%) of the title compound in the form of syn-isomer.

(2) Production of
7-[2-(2-aminothiazole-4-yl)-2-methoxyiminoacetamido]-2α-methyl-3-(1-methyl-1H-tetrazole-5-yl)thiomethyl-1-oxa-1-dethia-3-cephem-4-carboxylic acid trifluoroacetate (syn-isomer)

156 mg of the product from step (1) above was added under ice-cooling to the mixture of 2 ml of trifluoroacetic acid and 0.2 ml of anisole, followed by agitation for 30 minutes. The reaction solution obtained was admixed with 7 ml of isopropyl ether and the resulting precipitate was filtered off to afford 61 mg (72%) of the title compound in the syn-isomer form.

NMR (DMSO-d6), δ_ppm: 1.58 (3H, d, J=6.0 Hz, 2-CH3), 3.99 (3H, s, tetrazole 1-CH3), 3.85 (3H, s, —OCH3), 4.16 and 4.54 (each 1H, ABq, J=13.4 Hz, —CH2S—), 4.96 (1H, q, J=6.8 Hz, 2-H), 5.36 (1H, d, J=4 Hz, 6-H), 5.66 (1H, dd, J=9, 4 Hz, 7-H), 6.75 (1H, s, thiazole, 5-H).

EXAMPLE 9

(1) Preparation of (3R,4R)-4-{(1S)-1-ethoxycarbonylethoxy}-3-benzamido-1-(1-diphenylmethoxycarbonyl-2-methylprop-1-enyl)-azetidin-2-one (Compound A) and (3R,4R)-4-{(1R)-1-ethoxycarbonylethoxy}-3-benzamido-1-(1-diphenylmethoxycarbonyl-2-methylprop-1-enyl)azetidin-2-one 10 g of (1R,5S)-3-phenyl-6-(1-diphenylmethoxycarbonyl-2-methylprop-1-enyl)-7-oxo-4-oxa-2,6-diazabicyclo[3,2,0]hept-2-ene (see "Journal of Chemical Society", Perkin I, P. 1932, 1975) of the structure:

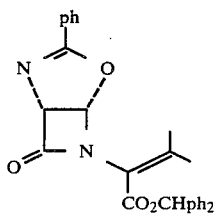

in which ph stands for phenyl group was dissolved in 35 ml of DL-α-lactic acid ethyl ester of the structure:

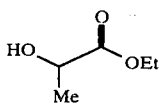

where Me is methyl and Et is ethyl group. To the solution was added 0.5 ml of trifluoromethanesulfonic acid and the mixture was stirred at ambient temperature for 1.5 hours to effect the ring-opening and condensation reactions of the starting compound. The reaction solution thus obtained was poured into 200 ml of aqueous sodium bicarbonate and allowed to stand for 30 minutes under ice-cooling.

The aqueous layer was removed to leave an oil, which was then taken up in 70 ml of ethyl acetate, washed with aqueous saturated sodium chloride and then with water, dried over MgSO4 and evaporated.

The residue containing the two diastereomers formed as the products was subjected to column chromatography on silica gel developed with benzene-ethyl acetate (7:1) to isolate the desired two diastereomers from each other, followed by crystallization from ethyl ether to give 2.1 g of Compound A of the structure:

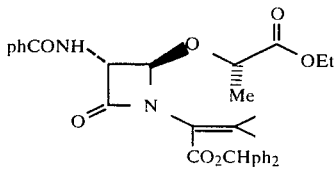

and 2.05 g of Compound B of the structure:

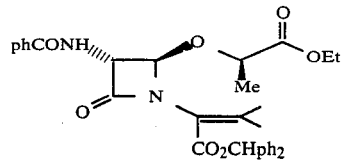

Properties of Compound A:
M.p.=104°–6° C.
[α]_D=−75° (c 1.0 in CHCl3)
IR (CHCl3), ν_max (cm⁻¹): 1763, 1738, 1661, 1602

Properties of Compound B:
M.p.=133°–5° C.
[α]_D=−2.1° (c 1.0 in CHCl3)
IR (CHCl3), ν_max (cm⁻¹): 1768, 1735, 1668, 1600

(2) Preparation of (3R,4R)-4-{(1R)-1-ethoxycarbonylethoxy}-3-benzamido-1-(1-diphenylmethoxycarbonyl-1-hydroxymethyl)azetidin-2-one 5.0 g of compound B obtained in step (1) above was dissolved in 150 ml of methylene chloride, and ozone was passed into the solution at −60° C. until the latter turned blue, thereby converting compound B into compound C of the structure:

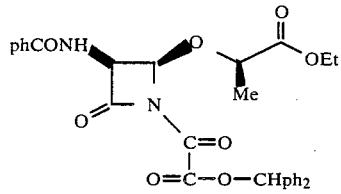

(see Reference Example 1(b)-(iv) given in the specification of our copending Japanese Patent Application No. 198466/81). To the reaction solution containing compound C were added at −60° C. 1 g of zinc powder and 1 ml of acetic acid, and the temperature of the mixture was raised to 0° C., followed by further addition of 10 g of zinc powder and 10 ml of acetic acid at that temperature. The resultant mixture was agitated for 30 minutes to allow the reductive reaction to take place.

The reaction mixture thus obtained was filtered and the filtrate was washed with aqueous saturated sodium bicarbonate and then with water, dried over MgSO4 and evaporated to give 4.3 g (90%) of the title compound having the structure:

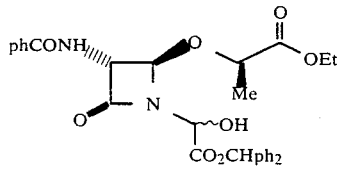

(3) Preparation of (3R,4R)-4-{(1R)-1-ethoxycarbonylethoxy}-3-benzamido-1-(1-diphenylmethoxycarbonyl-1-chloromethyl)azetidin-2-one 4.58 g of the product from step (2) above was dissolved in 50 ml of methylene chloride, and to the solution after ice-cooling were added 1.38 g of pyridine and 2.08 g of thionyl chloride, followed by agitation for 30 minutes to effect the chlorination.

The reaction solution was poured into ice water and the organic layer was separated off, washed with aqueous saturated sodium carbonate and then with water, dried over MgSO₄ and evaporated. There was thus obtained 4.50 g (95%) of the title compound having the structure:

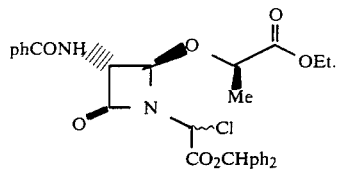

(4) Preparation of (3R,4R)-4-{(1R)-1-ethoxycarbonylethoxy}-3-benzamido-1-(1-diphenylmethoxycarbonyl-1-triphenylphosphoranylidenemethyl)azetidin-2-one 4.5 g of the product from step (3) above was dissolved in 50 ml of chloroform, to which were then added 1.46 ml of triethylamine and 4.5 g of triphenylphosphine (Pph₃), and the mixture was stirred at ambient temperature for 15 hours. The reaction solution was poured into 50 ml of ice water and adjusted to pH 3.

The organic layer was separated off, washed with aqueous saturated sodium bicarbonate and then with water, dried over MgSO₄ and evaporated under reduced pressure. The residue was purified by column chromatography on silica gel developed with a solvent of benzene-ethyl acetate (3:1) to afford 4.5 g (71%) of the title compound having the structure:

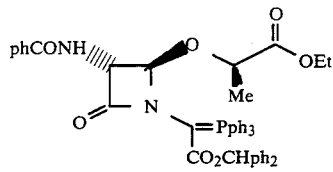

IR(CHCl₃), $\nu_{max}$ (cm$^{-1}$): 1764, 1732, 1652, 1612

(5) Preparation of (3R,4R)-4-{(1R)-1-carboxyethoxy}-3-benzamido-1-(1-diphenylmethoxycarbonyl-1-triphenylphosphoranylidenemethyl)azetidin-2-one 4.5 g of the product from step (4) above was dissolved in 70 ml of acetone, to which were then added 23 ml of water and 5.7 ml of aqueous 1N NaOH solution. The mixture was agitated at room temperature for 2 hours, followed by further addition of 2.8 ml of aqueous 1N NaOH solution and agitation at room temperature for 30 minutes to give rise to the hydrolysis.

The resultant reaction solution was adjusted to pH 7.0 and evaporated. The residue was triturated with isopropyl ether and filtered to give a powder, which was then suspended in a mixture of 50 ml of water and 50 ml of ethyl acetate. The suspension was adjusted to pH 2.0 with ice-cooling and the organic layer was separated, dried over MgSO₄ and evaporated to yield 4.16 g (96%) of the title compound having the structure:

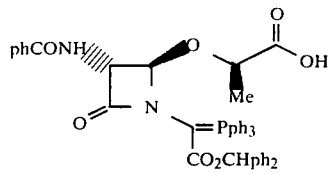

(6) Preparation of (3R,4R)-4-{(1R)-3-(1-methyl-1H-tetrazole-5-yl)thio-2-oxo-1-methylpropoxy)}-3-benzamido-1-(1-diphenylmethoxycarbonyl-1-triphenylphosphoranylidenemethyl)-azetidin-2-one (i) 3.29 g of the product from step (5) was dissolved in 40 ml of methylene chloride, to which were added at −10° C. 0.57 ml of N-methylmorpholine and 0.45 ml of ethyl chloroformate (Cl—COOEt). The mixture was allowed to react at that temperature under stirring for 30 minutes to produce the compound of the formula:

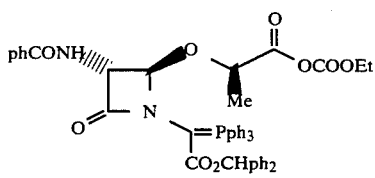

To the reaction solution comprising the above compound was added dropwise with ice-cooling 10 ml of ethyl ether containing 8 mmole of diazomethane. After completion of the addition the mixture was agitated for 30 minutes, whereby the diazomethylation took place to give a solution comprising the compound of the formula:

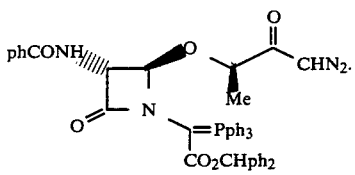

(ii) 1.43 ml of 6H HCl-dioxane solution was added dropwise with ice-cooling to the solution obtained in step (i) above, and the mixture was stirred at that temperature for 30 minutes to effect the chlorination. The resultant reaction solution was poured into 50 ml of ice water and the organic layer was separated off, washed with aqueous saturated sodium bicarbonate and then with water, dried over MgSO₄ and evaporated to give 3.10 g of an oil consisting essentially of the compound of the structure:

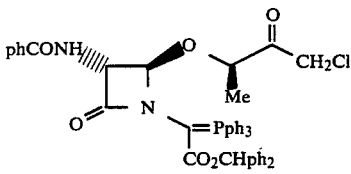

that is, (3R,4R)-4-{(1R)-3-chloro-2-oxo-1-methylpropoxy}-3-benzamido-1-(1-diphenylmethoxycarbonyl-1-triphenylphosphoranylidene-methyl)azetidin-2-one.

(iii) The oil was taken up in 50 ml of methylene chloride, to which were then added 0.60 g of 1-methyl-5-mercapto-1H-tetrazole and 0.47 ml of pyridine. The mixture was stirred at room temperature for 15 hours to effect the reaction for replacement of the chloro group by (1-methyl-tetrazole-5-yl)thio group. The reaction solution thus obtained was poured into 50 ml of ice water; the separated organic layer was then washed with aqueous saturated sodium bicarbonate and then with water, dried over MgSO₄ and evaporated. The residue was purified by column chromatography on silica gel developed with benzene-ethyl acetate (2:1) to afford 2.05 g (56%) of the title compound having the structure:

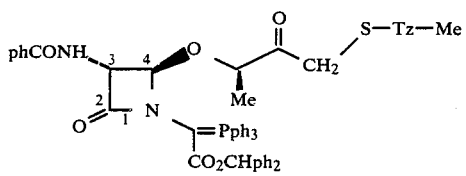

in which —Tz—Me stands for 1-methyl-tetrazole-5-yl group, that is, (3R,4R)-4-{(1R)-3-(1-methyl-1H-tetrazole-5-yl)thio-2-oxo-1-methylpropoxy}-3-benzamido-1-(1-diphenylmethoxycarbonyl-1-triphenylphosphoranylidenemethyl)-azetidin-2-one.

IR(CHCl₃), $\nu_{max}$ (cm⁻¹): 1766, 1730, 1653, 1615.

(7) Preparation of diphenylmethyl 7α-benzamido-2α-methyl-3-(1-methyl-1H-tetrazole-5-yl)thiomethyl-1-oxa-1-dethia-3-cephem-4-carboxylate 2.00 g of the final product obtained in step (6)(iii) above was dissolved in 75 ml of toluene, to which was added 50 mg of hydroquinone, and the mixture was heated under reflux for 9 hours to allow the cyclization to occur. The resultant reaction solution was evaporated and the residue was purified by column chromatography on silica gel with a developing solvent of benzene-ethyl acetate (3:1) to give 1.17 g (86%) of the title compound having the structure:

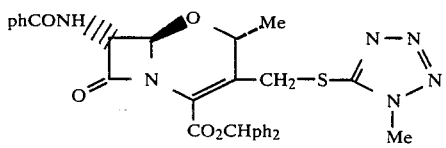

IR(CHCl₃), $\nu_{max}$ (cm⁻¹): 1787, 1718, 1672, 1600 NMR(CDCl₃), $\delta_{ppm}$: 1.51 (3H, d, J=6.9 Hz, 2-CH₃), 3.81 (3H, s, tetrazole 1-CH₃), 4.17, 4.40 (2H, ABq, J=13 Hz, —CH₂S—), 4.80 (1H, q, J=6.9 Hz, 2-H), 4.81 (1H, dd, J=7.5, 1.0 Hz, 7-H), 5.28 (1H, d, J=1.0 Hz, 6-H), 6.94 (1H, s, —CHph₂), 7.10–8.70 (15H, m, C₆H₅, 3).

(8) Preparation of diphenylmethyl 7α-amino-2α-methyl-3-(1-methyl-1H-tetrazole-5-yl)thiomethyl-1-oxa-1-dethia-3-cephem-4-carboxylate 840 mg of PCl₅ dissolved in 24 ml of methylene chloride was admixed at 0° C. with 0.48 ml of pyridine, and the admixture was agitated at that temperature for 30 minutes. To the resultant reaction solution was added dropwise at 0° C. 12 ml of methylene chloride containing 1200 mg of the product from step (7) above. The mixture was then stirred at 0° C. for 30 minutes and then at 0°–25° C. for one hour and cooled to 0° C., followed by addition of 30 ml of methanol. The mixture so obtained was again stirred at 0° C. for 10 minutes and then at 0°–25° C. for 40 minutes to achieve the removal of the benzoyl group (phCO-). The reaction solution was poured into 60 ml of ice water, agitated for 30 minutes and then evaporated.

The residue was taken up in 30 ml of ethyl acetate, washed with aqueous saturated sodium bicarbonate and then with water, dried over MgSO₄ and evaporated. The residue was purified by column chromatography on silica gel developed with benzene-ethyl acetate (1:1) to afford 630 mg (65%) of the title compound having the structure:

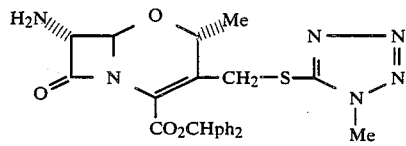

IR(CHCl₃), $\nu_{max}$ (cm⁻¹): 1779, 1713, 1620

(9) Preparation of diphenylmethyl 7α-(3,5-di-t-butyl-4-hydroxybenzylideneamino)-2α-methyl-3-(1-methyl-1H-tetrazole-5-yl)thiomethyl-1-oxa-1-dethia-3-cephem-4-carboxylate 600 mg of the product obtained in step (8) above and 312 mg of 3,5-di-t-butyl-4-hydroxybenzaldehyde were dissolved in 60 ml of benzene and the mixture was heated under reflux for 45 minutes in a Dean-Stark device. The resultant reaction solution was concentrated to dryness to yield 910 mg of the title compound having the structure:

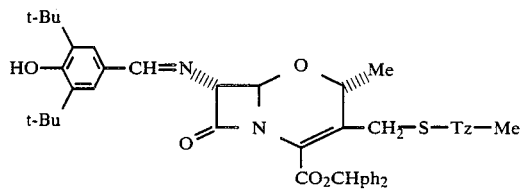

in which Me, Bu, ph and —Tz—Me represent, respectively, methyl, t-butyl, phenyl and 1-methyl-1H-tetrazole-5-yl groups.

(10) Preparation of diphenylmethyl 7β-(3,5-di-t-butyl-4-hydroxybenzylideneamino)-7α-methoxy-2α-methyl-3-(1-methyl-1H-tetrazole-5-yl)thiomethyl-1-oxa-1-dethia-3-cephem-4-carboxylate 910 mg of the product from step (9) above was dissolved in 15 ml of methylene chloride, to which were then added under ice-cooling 660 mg of MgSO₄ and 600 mg of nickel peroxide. The mixture was agitated at that temperature for 10 minutes to allow said product to oxidize into a benzoquinone-type intermediate of non-chiral form.

The reaction solution was then filtered and washed with 15 ml of methylene chloride. The washings and the filtrate were combined together, to which 30 ml of methanol was added under ice-cooling. The resulting mixture was stirred at that temperature for 30 minutes to give rise to the simultaneous reactions for the introduction of the 7α-methoxy group and for the rearrangement. The reaction solution thus obtained was concentrated to dryness to afford 900 mg of the title compound having the structure:

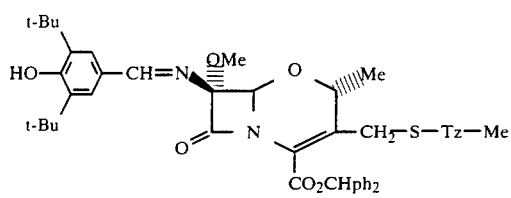

(11) Preparation of diphenylmethyl 7β-amino-7α-methoxy-2α-methyl-3-(1-methyl-1H-tetrazole-5-yl)thiomethyl-1-oxa-1-dethia-3-cephem-4-carboxylate To 900 mg of the product from step (10) above dissolved in 15 ml of ethyl acetate was added 15 ml of methanol containing 400 mg of Girard reagent T. The mixture was stirred at room temperature for 2 hours to effect the removal of the substituted benzylidene group from the 7β-amino group. The resultant reaction solution was evaporated and the residue was taken up in 20 ml of ethyl acetate. The solution was washed with water, dried over MgSO₄ and evaporated. The residue was purified by column chromatography on silica gel with a developing solvent of benzene-ethyl acetate (2:1) to give 405 mg (64%) of the title compound having the structure:

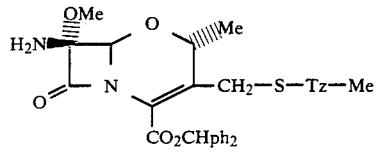

IR(CHCl$_3$), $\nu_{max}$ (cm$^{-1}$): 1782, 1720, 1603, NMR(CDCl$_3$), $\delta_{ppm}$: 1.55 (3H, d, J=6.8 Hz, 2-CH$_3$), 2.10 (2H, br, s, amino), 3.52 (3H, s, —OCH$_3$), 3.79 (3H, s, tetrazole 1-CH$_3$), 4.15, 4.48 (2H, ABq, J=14 Hz, —CH$_2$S—), 4.85 (1H, q, J=6.8 Hz, 2-H), 4.97 (1H, s, 6-H), 6.90 (1H, s, —CHph$_2$), 7.15–7.70 (10H, m, C$_6$H$_5$X2).

EXAMPLE 10

(1) Preparation of diphenylmethyl 7β-(3,5-di-t-butyl-4-hydroxybenzylideneamino)-2α-methyl-3-(1-methyl-1H-tetrazole-5-yl)thiomethyl-1-oxa-1-dethia-3-cephem-4-carboxylate 650 mg of the product from step (8) of Reference Example 1 was dissolved in 10 ml of methylene chloride, to which were then added under ice-cooling 470 mg of MgSO$_4$ and 460 mg of nickel peroxide. The mixture was agitated at that temperature for 10 minutes to allow said product to oxidize into a benzoquinone-type intermediate of nonchiral form. The reaction solution was then filtered and washed with 10 ml of methylene chloride. The washings and the filtrate were combined together and ice-cooled, followed by addition of 0.5 ml of methylene chloride containing 38 mg of tetraethylammonium borohydride. The mixture was stirred at that temperature for 10 minutes to cause the reduction. The resultant reaction solution was poured into 20 ml of ice water and adjusted to pH 5.0. The organic layer was separated off, washed with water, dried over MgSO$_4$ and evaporated to yield 630 mg of the title compound having the structure:

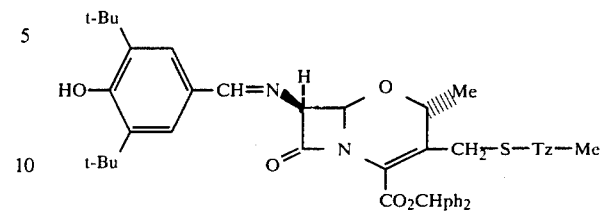

(2) Preparation of diphenylmethyl 7β-amino-2α-methyl-3-(1-methyl-1H-tetrazole-5-yl)thiomethyl-1-oxa-1-dethia-3-cephem-4-carboxylate To 630 mg of the product from step (1) above dissolved in 15 ml of ethyl acetate was added 10 ml of methanol containing 290 mg of Girard reagent T. The mixture was stirred at room temperature for one hour to effect the removal of the substituted benzylidene group from the 7β-amino group. The resultant reaction solution was evaporated and the residue was taken up in 20 ml of ethyl acetate. The solution was washed with water, dried over MgSO$_4$ and evaporated. The residue was purified by column chromatography on silica gel with a developing solvent of benzene-ethyl acetate (1:1) to give 151 mg (35%) of the title compound having the structure:

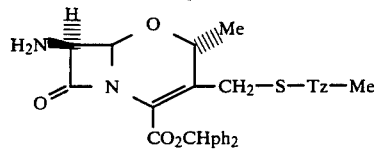

IR(CHCl$_3$), $\nu_{max}$ (cm$^{-1}$): 1785, 1720, 1602, NMR(CDCl$_3$), $\delta_{ppm}$: 1.57 (3H, d, J=6.8 Hz, 2-CH$_3$), 2.06 (2H, br.s, amino), 3.82 (3H, s, tetrazole, 1-CH$_3$), 4.21, 4.46 (2H, ABq, J=14 Hz), 4.55 (1H, d, J=4.5 Hz, 7-H), 4.86 (1H, q, J=6.8 Hz, 2-H), 5.15 (1H, d, J=4.5 Hz, 6-H), 6.92 (1H, s, —CHph$_2$), 7.15–7.70 (10H, m, C$_6$H$_5$X2).

EXAMPLE 11

(1) Preparation of diphenylmethyl 7α-benzamido-2β-methyl-3-(1-methyl-1H-tetrazole-5-yl)thiomethyl-1-oxa-1-dethia-3-cephem-4-carboxylate 2.70 Grams of (3R,4R)-4-{(1S)-3-(1-methyl-1H-tetrazole-5-yl)thio-2-oxo-1-methylpropoxy}-3-benzamido-1-(1-diphenylmethoxycarboxyl-1-triphenylphosphoranylidenemethyl)azetidin-2-one of the formula:

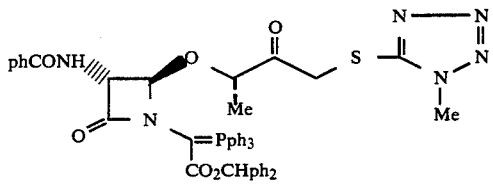

was dissolved in 270 ml of toluene to which was then added 180 mg of hydroquinone. The mixture was heated under reflux for 20 hours under a nitrogen atmosphere. The resultant reaction solution was concentrated and the residue was purified by a column chromatography on silica gel developed with benzene-ethyl acetate (4:1) to give 1.50 g (81%) of the title compound having the structure:

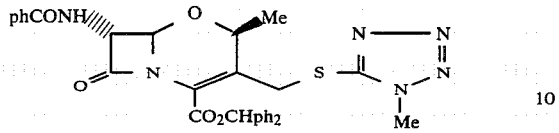

IR (CHCl$_3$), $\nu_{max}$ (cm$^{-1}$): 1780, 1718, 1668, 1600

NMR (CDCl$_3$), $\delta_{ppm}$: 1.51 (3H, d, J=6.8 Hz, 2-CH$_3$), 3.79 (3H, s, tetrazole 1-CH$_3$), 4.03, 4.66 (2H, ABq, J=14 Hz, —CH$_2$S—), 4.80 (1H, q, J=6.8 Hz, 2-H), 4.89 (1H, dd, J=7, 1 Hz, 7-H), 5.10 (1H, d, J=1 Hz, 6-H), 6.85 (1H, d, J=7 Hz, —CONH—), 6.92 (1H, s, —CHph$_2$), 7.10–8.90 (15H, m, C$_6$H$_5$ x3).

(2) Preparation of diphenylmethyl 7α-amino-2β-methyl-3-(1-methyl-1H-tetrazole-5-yl)thiomethyl-1-oxa-1-dethia-3-cephem-4-carboxylate Pyridine (0.48 ml) was added at 0° C. to 843 mg of PCl$_5$ which was dissolved in 24 ml of methylene chloride, and the mixture was stirred at that temperature for 30 minutes. To the solution thus obtained was added dropwise at 0° C. 15 ml of methylene chloride containing 1200 mg of the product obtained from the step (1) above. The mixture was agitated at that temperature for 30 minutes and at 0°–25° C. for further one hour and then cooled down to 0° C., followed by addition of 12 ml of methanol thereto. The mixture was again stirred at that temperature for 10 minutes and at 0°–25° C. for further 40 minutes.

The resultant reaction solution was poured into 50 ml of ice water, agitated for 30 minutes and then concentrated.

The residue was taken up in 30 ml of ethyl acetate, washed with saturated aqueous sodium bicarbonate and then with water, dried over MgSO$_4$ and concentrated.

The residue was purified by a column chromatography on silica gel using a developing solvent of benzene-ethyl acetate (1:1) to afford 500 mg (50%) of the title compound of the structure:

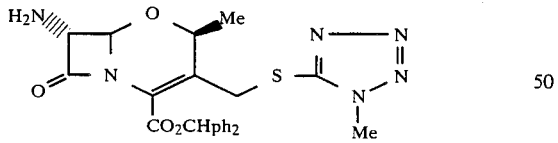

IR (CHCl$_3$), $\nu_{max}$ (cm$^{-1}$): 1778, 1723, 1608

NMR (CDCl$_3$), $\delta_{ppm}$: 1.49 (3H, d, J=6.8 Hz, 2-CH$_3$), 2.00 (2H, br. s, amino), 3.77 (3H, s, tetrazole 1-CH$_3$), 4.04, 4.63 (2H, ABq, J=14 Hz, —CH$_2$S—), 4.05 (1H, d, J=1 Hz, 7-H), 4.75 (1H, d, J=1 Hz, 6-H), 4.80 (1H, q, J=6.8 Hz, 2-H), 6.90 (1H, s, —CHph$_2$), 7.10–7.70 (10H, m, C$_6$H$_5$ x2).

(3) Preparation of diphenylmethyl 7α-(3,5-di-tert-butyl-4-hydroxybenzylideneamino)-2β-methyl-3-(1-methyl-1H-tetrazole-5-yl)thiomethyl-1-oxa-1-dethia-3-cephem-4-carboxylate The product (350 mg) obtained in the step (2) above and 184 mg of 3,5-di-tert-butyl-4-hydroxybenzaldehyde were dissolved in 100 ml of benzene, and the mixture was heated under reflux for 50 minutes in a Dean-Stark device. The resultant reaction solution was concentrated to yield 530 mg of the title compound having the structure:

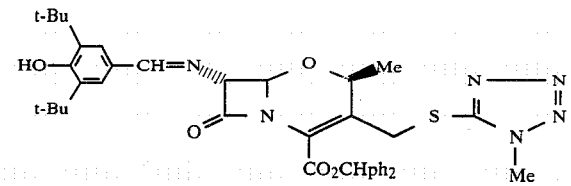

NMR (CDCl$_3$), ($\delta_{ppm}$): 1.47 (18 H, s, tert-butyl), 1.57 (3H, d, J=6.8 Hz, 2-CH$_3$), 3.80 (3H, s, tetrazole 1-CH$_3$), 4.08, 4.68 (2H, ABq, J=14 Hz, —CH$_2$S—), 4.71 (1H, br. s, 7-H), 4.82 (1H, q, J=6.8 Hz, 2-H), 5.16 (1H, d, J=1 Hz, 6-H), 5.56 (1H, s, —OH), 6.90 (1H, s, —CHph$_2$), 7.10 7.75 (10H, m, C$_6$H$_5$ x2), 7.60 (2H, s, C$_6$H$_5$), 8.35 (1H, d, J=1 Hz, —CH=N—)

(4) Preparation of diphenylmethyl 7β-(3,5-di-tert-butyl-4-hydroxybenzylideneamino)-2β-methyl-3-(1-methyl-1H-tetrazole-5-yl)thiomethyl-1-oxa-1-dethia-3-cephem-4-carboxylate The product (327 mg) of the step (3) above was dissolved in 5 ml of methylene chloride, to which were then added under ice-cooling 236 mg of MgSO$_4$ and 236 mg of nickel peroxide. The mixture was agitated at that temperature for 10 minutes and then the reaction solution was filtered and the filtration residue was washed with 5 ml of methylene chloride. The washings and the filtrate were combined together.

The resultant solution was ice-cooled, followed by addition of 0.1 ml of methylene chloride containing 16 mg of tetraethylammonium borohydride. The resulting mixture was stirred at that temperature for 10 minutes and poured into 10 ml of ice water, so that the inversion reaction took place at the 7-position. The reaction mixture was then adjusted to pH 5.0. The organic layer was separated, washed with water, dried over MgSO$_4$ and concentrated to afford 309 mg of the title compound having the structure:

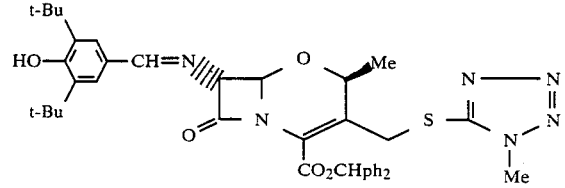

(5) Preparation of diphenylmethyl 7β-amino-2β-methyl-3-(1-methyl-1H-tetrazole-5-yl)thiomethyl-1-oxa-1-dethia-3-cephem-4-carboxylate The product (309 mg) obtained from the step (4) above which are dissolved in 5 ml of ethyl acetate was added 5 ml of methanol containing 145 mg of Girard T reagent. The mixture was stirred at room temperature for one hour, and then the resultant reaction solution was concentrated.

The residue was taken up in 20 ml of ethyl acetate, and the solution was washed with water, dried over MgSO$_4$ and evaporated.

The residue was purified by a column chromatography on silica gel with a developing solvent of benzene-ethyl acetate (1:1) to give 66 mg (31%) of the title compound having the structure:

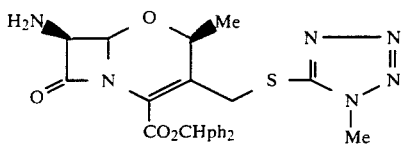

m.p. 131°–133° C. (decomp.)

IR (CHCl₃), $\nu_{max}$ (cm⁻¹): 1783, 1720, 1602

NMR (CDCl₃), $\delta_{ppm}$: 1.53 (3H, d, J=6.8 Hz, 2-CH₃), 2.12 (2H, br. s, amino), 3.79 (3H, s, tetrazole 1-CH₃), 4.02, 4.67 (2H, ABq, J=14 Hz, —CH₂S—), 4.45 (1H, d, J=5 Hz, 7-H), 4.80 (1H, q, J=6.8 Hz, 2-H), 4.97 (1H, d, J=5 Hz, 6-H), 6.84 (1H, s, —CHph₂), 7.10–7.65 (10H, m, C₆H₅ x2).

EXAMPLE 12

(1) Preparation of diphenylmethyl 7β-(3,5-di-tert-butyl-4-hydroxybenzylideneamino)-7α-methoxy-2β-methyl-3-(1-methyl-1H-tetrazole-5-yl)thiomethyl-1-oxa-1-dethia-3-cephem-4-carboxylate The product (530 mg) obtained from the step (4) of Example 11 was dissolved in 8 ml of methylene chloride, to which were then added under ice-cooling 380 mg of MgSO₄ and 300 mg of nickel peroxide. The mixture was agitated at that temperature for 10 minutes, then filtered and the filtration residue was washed with 8 ml of methylene chloride. The washings and the filtrate were combined together.

To the filtrate was then added under ice-cooling 10 ml of methanol. The resulting mixture was stirred at that temperature for 30 minutes to give rise to the simultaneous reactions for introduction of the 7α-methoxy group and for the inversion. The reaction solution thus obtained was concentrated to afford 490 mg of the title compound having the structure:

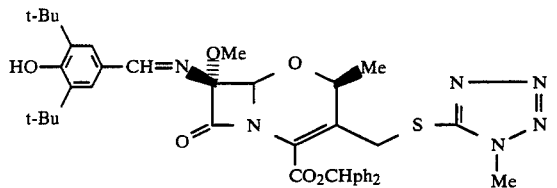

NMR (CDCl₃), $\delta_{ppm}$: 1.33 (3H, d, J=6.8 Hz, 2-CH₃), 1.47 (18H, s, tert-butyl), 3.59 (3H, s, —OCH₃), 3.80 (3H, s, tetrazole 1-CH₃), 4.07, 4.70 (2H, ABq, J=14 Hz, —CH₂S—), 4.77 (1H, q, J=6.8 Hz, 2-H), 5.08 (1H, s, 6-H), 5.59 (1H, s, —OH), 6.91 (1H, s, —CHph₂), 7.10–7.80 (10H, m, C₆H₅ x2), 6.66 (2H, s, C₆H₅), 8.44 (1H, s, —CH=N—)

(2) Preparation of diphenylmethyl 7β-amino-7α-methoxy-2β-methyl-3-(1-methyl-1H-tetrazole-5-yl)thiomethyl-1-oxa-1-dethia-3-cephem-4-carboxylate The product (490 mg) of the step (1) above which was dissolved in 8 ml of ethyl acetate was added 8 ml of methanol containing 240 mg of Girard T reagent. The mixture was stirred at room temperature for 1.5 hours and then concentrated.

The residue was taken up in 10 ml of ethyl acetate, and the solution was washed with water, dried over MgSO₄ and concentrated.

The residue was purified by a column chromatography on silica gel with a developing solvent of benzene-ethyl acetate (2:1) to give 241 mg (65%) of the title compound having the structure:

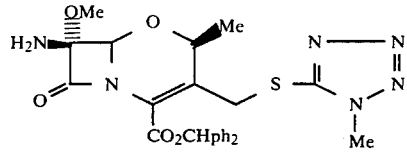

m.p. 133°–5° C. (decomp.)

IR (CHCl₃), $\nu_{max}$ (cm⁻¹): 1783, 1720, 1600

NMR (CDCl₃), $\delta_{ppm}$: 1.53 (3H, d, J=6.8 Hz, 2-CH₃), 2.16 (2H, br.s, amino), 3.49 (3H, s, —OCH₃), 3.79 (3H, s, tetrazole 1-CH₃), 4.03, 4.62 (2H, ABq, J=14 Hz, —CH₂S—), 4.83 (1H, q, J=6.8 Hz, 2-H), 4.85 (1H, S, 6-H), 6.86 (1H, s, —CHph₂), 7.10–7.70 (10H, m, C₆H₅ x2).

EXAMPLE 13

(1) Preparation of diphenylmethyl 7α-benzamido-2α-methyl-3-(2-methyl-1,3,4-thiadiazole-5-yl)thiomethyl-1-oxa-1-dethia-3-cephem-4-carboxylate 1.70 Grams of (3R,4R)-4-{(1R)-3-(2-methyl-1,3,4-thiadiazole-5-yl)thio-2-oxo-1-methylpropoxy}-3-benzamido-1-(1-diphenylmethoxycarbonyl-1-triphenylphosphoranylidenemethyl)azetidin-2-one was dissolved in 30 ml of toluene, to which was then added 100 mg of hydroquinone. The mixture was heated under reflux for 10 hours under a nitrogen atmosphere. The resultant reaction solution was concentrated, and the residue was purified by a column chromatography on silica gel with a developing solvent of benzene-ethyl acetate (3:1) to afford 0.95 g (81%) of the title compound having the structure:

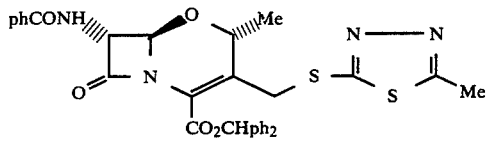

IR (CHCl₃), $\nu_{max}$ (cm⁻¹): 1784, 1719, 1668, 1600

NMR (CDCl₃), $\delta_{ppm}$: 1.48 (3H, d, J=6.8 Hz, 2-CH₃), 2.68 (3H, s, thiadiazole 2-CH₃), 4.31 (2H, br.s, —CH₂S—), 4.79 (1H, q, J=6.8 Hz, 2-H), 4.90 (1H, dd, J=8.9 1 Hz, 7-H), 5.24 (1H, d, J=1 Hz, 6-H), 6.94 (1H, s, —CHph₂), 7.10–7.85 (15H, m, C₆H₅ x3).

EXAMPLE 14

(1) Preparation of diphenylmethyl 7α-benzamido-2β,3-dimethyl-1-oxa-1-dethia-3-cephem-4-carboxylate (3R,4R)-4-{(1S)-2-Oxo-1-methylpropoxy}-3-benzamido-1-(1-diphenylmethoxycarbonyl-1-phosphoranylidenemethyl)azetidin-2-one (100 mg) was dissolved in 10 ml of dioxane, and the solution was heated under reflux for 52 hours in a nitrogen atmosphere. The resultant reaction solution was concentrated.

The residue was purified by a column chromatography on silica gel to give 20 mg (32%) of the title compound of the structure:

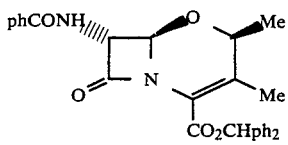

NMR (CDCl$_3$), $\delta_{ppm}$: 1.42 (3H, d, J=6.8 Hz, 2-CH$_3$), 1.95 (3H, s, 3-CH$_3$), 4.32 (1H, q, J=6.8 Hz, 2-H), 4.94 (1H, dd, J=7, 1 Hz, 7-H), 4.97 (1H, d, J=1 Hz, 6-H), 6.90 (1H, s, —CHph$_2$), 7.00–7.80 (15H, m, C$_6$H$_5$ x3).

(2) Preparation of diphenylmethyl 7α-amino-2β,3-dimethyl-1-oxa-1-dethia-3-cephem-4-carboxylate Pyridine (1.0 ml) was added at 0° C. to 1750 mg of PCl$_5$ which was dissolved in 45 ml of methylene chloride, and the mixture was stirred at that temperature for 30 minutes. To the solution thus obtained was added dropwise at 0° C. 15 ml of methylene chloride containing 2030 mg of the product obtained from the step (1) above. The mixture was agitated at that temperature for 30 minutes and at 0°–25° C. for further one hour. The mixture was then cooled down to 0° C., followed by addition of 25 ml of methanol. The admixture was again stirred at that temperature for one hour and at 0°–25° C. for further one hour. The resultant reaction solution was poured into 50 ml of ice water, agitated for 30 minutes and then concentrated.

The residue was taken up in 50 ml of ethyl acetate, washed with saturated aqueous sodium bicarbonate and then with water, dried over MgSO$_4$ and concentrated.

The residue was purified by a column chromatography on silica gel using a developing solvent of benzene-ethyl acetate (2:1) to afford 960 mg (60%) of the title compound of the structure:

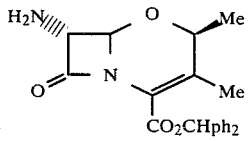

IR (CHCl$_3$), $\nu_{max}$ (cm$^{-1}$): 1770, 1718

NMR (CDCl$_3$), $\delta_{ppm}$: 1.37 (3H, d, J=6.8 Hz, 2-CH$_3$), 1.84 (2H, s, H$_2$N—), 1.91 (3H, d, J=0.9 Hz, 3-CH$_3$), 4.01 (1H, s, 7-H), 4.35 (1H, q, J=6.8 Hz, 2-H), 4.72 (1H, s, 6-H), 6.92 (1H, s, —CHph$_2$), 7.10–7.60 (10H, m, C$_6$H$_5$ x2).

(3) Preparation of diphenylmethyl 7α-(3,5-di-tert-butyl-4-hydroxybenzylideneamino)-2β,3-dimethyl-1-oxa-1-dethia-3-cephem-4-carboxylate The product (960 mg) obtained in the step (2) above and 654 mg of 3,5-di-t-butyl-4-hydroxybenzaldehyde were dissolved in 50 ml of benzene, and the mixture was heated under reflux for one hour in a Dean-Stark device. The resultant reaction solution was concentrated to yield 1500 mg of the title compound having the structure:

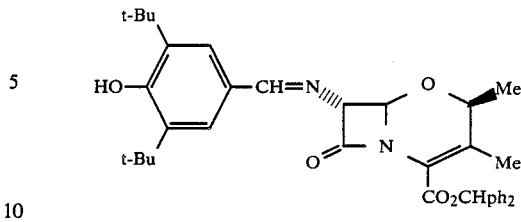

IR (CHCl$_3$), $\nu_{max}$ (cm$^{-1}$): 1770, 1719, 1680

NMR (CDCl$_3$), $\delta_{ppm}$: 1.41 (3H, d, J=6.8 Hz, 2-CH$_3$), 1.46 (18H, s, tert-Bu), 1.97 (3H, d, J=0.9 Hz, 3-CH$_3$), 4.44 (1H, q, J=6.8 Hz, 2-H), 4.70 (1H, br.s, 7-H), 5.13 (1H, br.s, 6-H), 5.58 (1H, s, —OH), 6.90 (1H, s, —CHph$_2$), 7.10–7.70 (10H, m, C$_6$H$_5$ x2), 7.64 (2H, s, C$_6$H$_2$), 8.41 (1H, d, J=1.5 Hz, —CH=N—).

(4) Preparation of diphenylmethyl 7β-(3,5-di-t-butyl-4-hydroxybenzylideneamino)-2β,3-dimethyl-1-oxa-1-dethia-3-cephem-4-carboxylate The product (1400 mg) of the step (3) above was dissolved in 30 ml of methylene chloride, to which were then added under ice-cooling 950 mg of MgSO$_4$ and 950 mg of nickel peroxide, and the mixture was agitated at that temperature for 10 minutes. The reaction solution was then filtered and the filtration residue was washed with 30 ml of methylene chloride. The washings and the filtrate were combined together.

The filtrate was cooled to −20° C., followed by addition of 2 ml of methylene chloride containing 100 mg of tetraethylammonium berohydride. The mixture so obtained was stirred at that temperature for ten minutes and then poured into 50 ml of ice water.

The reaction mixture was adjusted to pH 5.0, and the organic layer was separated, washed with water, dried over MgSO$_4$ and concentrated to yield 1200 mg of the title compund having the structure:

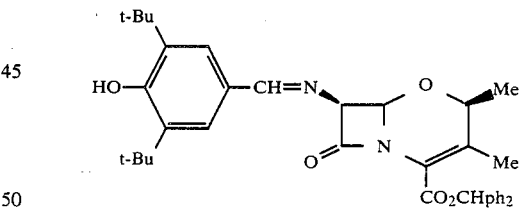

(5) Preparation of diphenylmethyl 7β-amino-2β,3-dimethyl-1-oxa-1-dethia-3-cephem-4-carboxylate To 1200 mg of the product of the step (4) above which was dissolved in 14 ml of ethyl acetate was added 14 ml of methanol containing 600 mg of Girard T reagent. The mixture was stirred at room temperature for one hour and then concentrated.

The residue was taken up in 45 ml of ethyl acetate, and the solution was washed with water, dried over MgSO$_4$ and concentrated.

The residue was purified by a column chromatography on silica gel with a developing solvent of benzene-ethyl acetate (1:1) to give 488 mg (64%) of the title compound having the structure:

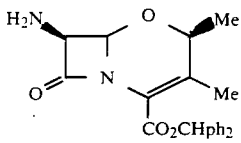

IR (CHCl₃), $v_{max}$ (cm⁻¹): 1778, 1718
NMR (CDCl₃), $\delta_{ppm}$: 1.41 (3H, d, J=6.8 Hz, 2-CH₃), 1.84 (2H, br.s, H₂N—), 1.98 (3H, d, J=0.9 Hz, 3-CH₃), 4.40 (1H, q, J=6.8 Hz, 2-H), 4.45 (1H, d, J=4.0 Hz, 7-H), 4.98 (1H, d, J=4.0 Hz, 6-H), 6.89 (1H, s, —CHph₂), 7.10–7.60 (10H, m, C₆H₅ x2).

EXAMPLE 15

(1) Preparation of diphenylmethyl 7α-benzamido-2α,3-dimethyl-1-oxa-1-dethia-3-cephem-4-carboxylate (3R,4R)-4-{(1R)-2-Oxo-1-methylproxy}-3-benzamido-1-(1-diphenylmethoxycarbonyl-1-phosphoranylidenemethyl)azetidin-2-one (1.30 g) was dissolved in 120 ml of toluene, to which was added 70 ml of hydroquinone, and the mixture was heated under reflux for 40 hours in a nitrogen atmosphere. The resultant reaction solution was concentrated.

The residue was purified by a column chromatography on silica gel to give 0.43 g (52%) of the title compound of the structure:

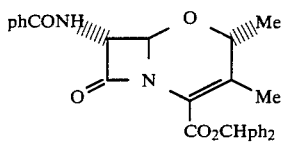

IR (CHCl₃), $v_{max}$ (cm⁻¹): 1770, 1718, 1660
NMR (CDCl₃), $\delta_{ppm}$: 1.38 (3H, d, J=6.9 Hz, 2-CH₃), 2.02 (3H, s, 3-CH₃), 4.42 (1H, q, J=6.9 Hz, 2-H), 4.99 (1H, dd, J=7.6, 1 Hz, 7-H), 5.13 (1H, s, 6-H), 6.91 (1H, s, —CHph₂), 7.00–7.90 (15H, m, C₆H₅ x3).

(2) Preparation of diphenylmethyl 7α-amino-2α,3-dimethyl-1-oxa-1-dethia-3-cephem-4-carboxylate Pyridine (1.0 ml) was added at 0° C. to 1720 mg of PCl₅ which was dissolved in 40 ml of methylene chloride, and the mixture was stirred at that temperature for 30 minutes. To the solution thus obtained was added dropwise at 0° C. 15 ml of methylene chloride containing 2000 mg of the product of the step (1) above. The mixture was agitated at that temperature for 30 minutes and at 0°–25° C. for further one hour. The mixture was then cooled to 0° C., followed by addition of 25 ml of methanol. The mixture was again stirred at that temperature for one hour and at 0°–25° C. for further one hour. The resultant reaction solution was poured into 40 ml of ice water, agitated for 30 minutes and then concentrated.

The residue was taken up in 50 ml of ethyl acetate, washed with saturated aqueous sodium bicarbonate and then with water, dried over MgSO₄ and concentrated.

The residue was purified by a column chromatography on a silica gel using a developing solvent of benzene-ethyl acetate (2:1) to afford 1035 mg (66%) of the title compound of the structure:

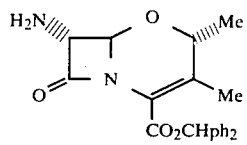

IR (CHCl₃), $v_{max}$ (cm⁻¹): 1773, 1720
NMR (CDCl₃), $\delta_{ppm}$: 1.40 (3H, d, J=6.9 Hz, 2-CH₃), 1.88 (2H, br.s, —NH₂), 2.01 (3H, s, 3-CH₃), 4.02 (1H, br.s, 7-H), 4.37 (1H, q, J=6.9 Hz, 2-H), 4.87 (1H, br.s, 6-H), 6.93 (1H, s, —CHph₂), 7.10–7.60 (10H, m, C₆H₅ x2).

(3) Preparation of diphenylmetnyl 7α-(3,5-di-tert-butyl-4-hydroxybenzylideneamino)-2α,3-dimethyl-1-oxa-1-dethia-3-cephem-4-carboxylate The product (1000 mg) obtained in the step (2) above and 680 mg of 3,5-di-tert-butyl-4-hydroxybenzaldehyde were dissolved in 50 ml of benzene, and the mixture was heated under reflux for one hour in a Dean-Stark device. The resultant reaction solution was concentrated to yield 1571 mg of the title compound.

IR (CHCl₃), $v_{max}$ (cm⁻¹): 1775, 1720, 1682
NMR (CDCl₃), $\delta_{ppm}$: 1.40 (3H, d, J=6.9 Hz, 2-CH₃), 1.46 (18H, s, tert-Bu), 2.05 (3H, s, 3-CH₃), 4.43 (1H, q, J=6.9 Hz, 2-H), 4.68 (1H, br.s, 7-H), 5.27 (1H, s, 6-H), 5.57 (1H, s, —OH), 6.92 (1H, s, —CHph₂), 7.10–7.70 (10H, m, C₆H₅ x2), 7.60 (2H, s, —C₆H₂), 8.41 (1H, d, 1.5 Hz, —CH=N—).

(4) Preparation of diphenylmethyl 7β-(3,5-di-tert-butyl-4-hydroxybenzylideneamino)-2α,3-dimethyl-1-oxa-1-dethia-3-cephem-4-carboxylate The product (1500 mg) of the step (3) above was dissolved in 30 ml of methylene chloride, to which were then added under ice-cooling 970 mg of MgSO₄ and 970 mg of nickel peroxide, and the mixture was agitated at that temperature for 10 minutes. The reaction solution was then filtered and the filtration residue was washed with 30 ml of methylene chloride. The washings and the filtrate were combined together.

The filtrate was then cooled to −20° C., followed by addition of 2 ml of methylene chloride containing 110 mg of tetraethylammonium borohydride. The mixture so obtained was stirred at that temperature for ten minutes and then poured into 50 ml of ice water.

The reaction mixture was adjusted to pH 5.0, and the organic layer was separated, washed with water, dried over MgSO₄ and concentrated to yield 1400 mg of the title compound having the structure:

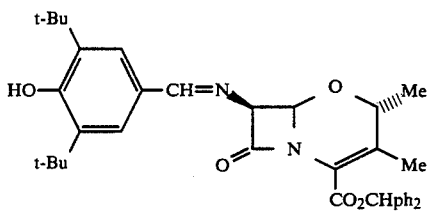

(5) Preparation of diphenylmethyl 7β-amino-2α,3-dimethyl-1-oxa-1-dethia-3-cephem-4-carboxylate To the product (1400 mg) of the step (4) above which was dissolved in 15 ml of ethyl acetate was added 15 m of methanol containing 690 mg of Girard T reagent. The mixture was stirred at room temperature for one hour and then concentrated.

The residue was taken up in 50 ml of ethyl acetate, and the solution was washed with water, dried over MgSO₄ and concentrated.

The residue was purified by a column chromatography on silica gel developed with benzene-ethyl acetate (1:1) to afford 587 mg (66%) of the title compound of the structural formula:

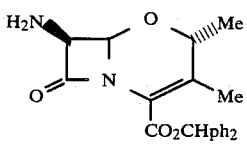

IR (CHCl₃), $\nu_{max}$ (cm⁻¹): 1782, 1719, 1600

NMR (CDCl₃), $\delta_{ppm}$: 1.44 (3H, d, J=6.9 Hz, 2-CH₃), 1.86 (2H, br.s, —NH₂), 2.06 (3H, s, 3-CH₃), 4.44 (1H, q, J=6.9 Hz, 2-H), 4.49 (1H, d, J=3.8 Hz, 7-H), 5.13 (1H, d, J=3.8 Hz, 6-H), 6.90 (1H, s, —CHph₂), 7.10-7.70 (10H, m, C₆H₅ x2).

EXAMPLE 16

(1) Preparation of diphenylmethyl 7α-benzamido-2α-methyl-3-chloromethyl-1-oxa-1-dethia-3-cephem-4-carboxylate 1.59 Grams of (3R,4R)-4-{(1R)-3-chloro-2-oxo-1-methylpropoxy}-3-benzamido-1-(1-diphenylmethoxycarbonyl-1-triphenylphosphoranylidenemethyl)azetidin-2-one of the formula:

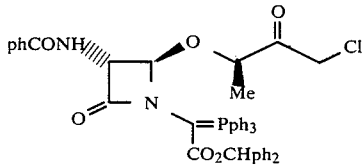

was dissolved in 50 ml of toluene. The solution was heated under reflux for 3 hours and then concentrated.

The residue was purified by a column chromatography on silica gel developed with benzene-ethyl acetate (5:1) to give 0.70 g (68%) of the title compound having the structure:

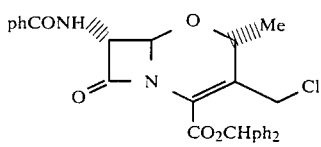

IR (CHCl₃), $\nu_{max}$ (cm⁻¹): 1786, 1728, 1663, 1602.
NMR (CDCl₃), $\delta_{ppm}$: 1.46 (3H, d, J=6.9 Hz, 2-CH₃), 4.22, 4.53 (2H, ABq, J=11.5 Hz, —CH₂Cl), 4.78 (1H, q, J=6.9 Hz, 2-H), 4.95 (1H, dd, J=7.5, 1 Hz, 7-H), 5.23 (1H, d, J=1 Hz, 6-H), 6.95 (1H, s, —CHph₂), 7.00-7.90 (15H, m, C₆H₅ x3).

(2) Preparation of diphenylmethyl 7α-benzamido-2α-methyl-3-(1,3,4-thiadiazole-5-yl)thiomethyl-1-oxa-1-dethia-3-cephem-4-carboxylate The product (800 mg) of the step (1) above was dissolved in 20 ml of methylene chloride, to which was then added 10 ml of an aqueous solution containing 220 mg of 5-mercapto-1,3,4-thiadiazole, 260 mg of NaHCO₃ and 70 mg of tetraethylammonium chloride. The resultant mixture was agitated at room temperature for 2 hours. The organic layer was separated, washed with water, dried and concentrated. The residue was purified by a column chromatography on silica gel with a developing solvent of benzene-ethyl acetate (3:1) to give 580 mg (63%) of crystals of the title compound having the structure:

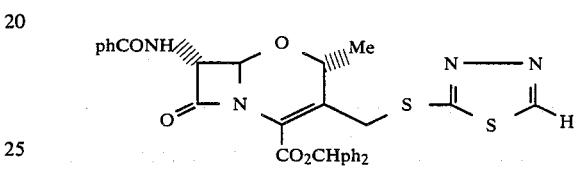

m.p. 170°-172° C. (decomp.)
IR (CHCl₃), $\nu_{max}$ (cm⁻¹): 1782, 1718, 1665, 1600.
NMR (CDCl₃), $\delta_{ppm}$: 1.52 (3H, d, J=6.8 Hz, 2-CH₃), 4.41 (2H, br.s, —CH₂S—), 4.82 (1H, q, J=6.8 Hz, 2-H), 4.90 (1H, dd, J=7, 1 Hz, 7-H), 5.26 (1H, d, J=1 Hz, 6-H), 6.96 (1H, s, —CHph₂), 7.06 (1H, d, J=7.1 Hz, —CONH—), 7.10-7.90 (15H, m, C₆H₅ x3), 8.96 (1H, s, thiadiazole 2-H)

EXAMPLE 17

(1) Preparation of (3R,4R)-4-{(1S)-1-ethoxycarbonylethoxy}-3-benzamido-1-(1-diphenylmethoxycarbonyl-1-hydroxymethyl)-azetidin-2-one 3.0 Grams of the compound (a) obtained in the step (1) of Example 9 was dissolved in 150 ml of methylene chloride, and ozone was passed into the solution at −60° C. until the latter turned blue. To the reaction solution were added at −60° C. 1 g of zinc powder and 1 ml of acetic acid, and the temperature of the mixture was raised to 0° C., followed by further addition of 6.8 g of zinc powder and 6.3 ml of acetic acid at that temperature, and the mixture was agitated for 30 minutes.

The reaction mixture thus obtained was filtered and the filtrate was washed with saturated aqueous sodium bicarbonate and then with water, dried over MgSO₄ and concentrated to give 2.75 (96%) of the title compound having the structure:

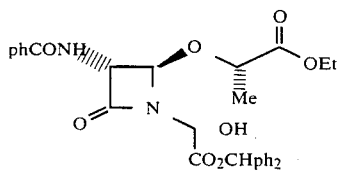

IR (CHCl₃), $\nu_{max}$ (cm⁻¹): 3420, 1781, 1735, 1660, 1600.
NMR (CDCl₃), $\delta_{ppm}$: 1.18, 1.21 (3H, t, —CH₂CH₃), 1.18, 1.48 (3H, d, —CHCH₃), 4.03, 4.12 (2H, q, —CH$_2$CH$_3$), 4.33, 4.43 (1H, q, —CHCH$_3$), 4.75, 4.80 (1H, dd, 3-H), 4.90, 4.99 (1H, d, 4-H), 5.40, 5.53 (1H, br.s, —CHOH), 6.86, 6.92 (1H, s, —CHph$_2$), 7.60–7.80 (15H, m, C$_6$H$_5$ x3).

(2) Preparation of (3R,4R)-4-{(1S)-1-ethoxycarbonylethoxy}-3-benzamido-1-(1-diphenylmethoxycarbonyl-1-chloromethyl)azetidin-2-one 2.75 Grams of the product of the step (1) above was dissolved in 50 ml of methylene chloride, and to the solution after ice-cooling were added 1.24 g of pyridine and 1.87 g of thionyl chloride, followed by agitation for 30 minutes.

The reaction solution was poured into ice water and the organic layer was separated, washed with saturated aqueous sodium carbonate and then with water, dried over MgSO$_4$ and concentrated. There was thus obtained 2.64 g (93%) of the title compound.

IR (CHCl$_3$), $\nu_{max}$ (cm$^{-1}$); 1785, 1738, 1666, 1605

NMR (CDCl$_3$), $\delta_{ppm}$: 1.22 (3H, t, —CH$_2$CH$_3$), 1.37, 1.47 (3H, d, —CHCH$_3$) 4.12 (2H, q, —CH$_2$CH$_3$), 4.44 (1H, q, —CHCH$_3$), 4.73 (1H, dd, 3-H), 5.32, 5.37 (1H, d, 4-H), 6.17, 6.21 (1H, s, —CHCl), 6.87, 6.92 (1H, s, —CHph$_2$), 7.10–7.70 (15H, m, C$_6$H$_5$ x3).

(3) Preparation of (3R,4R)-4-{(1S)-1-ethoxycarbonylethoxy}-3-benzamido-1-(1-diphenylmethoxycarbonyl-1-triphenylphosphoranylidenemethyl)azetidin-2-one 2.64 Grams of the product of the step (2) above was dissolved in 50 ml of chloroform, to which were then added 0.75 ml of triethylamine and 2.75 g of triphenylphosphine. The mixture was stirred at ambient temperature for 15 hours. The reaction solution was poured into 50 ml of ice water and adjusted to pH 3. The organic layer was separated, washed with saturated aqueous sodium bicarbonate and then with water, dried over MgSO$_4$ and then concentrated.

The residue was purified by a column chromatography on silica gel developed with a solvent of benzene-ethyl acetate (3:1) to afford 2.50 g (67%) of the title compound having the structure:

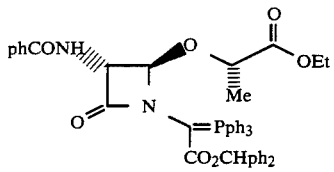

IR (CHCl$_3$), $\nu_{max}$ (cm$^{-1}$): 1761, 1739, 1655, 1615

(4) Preparation of (3R,4R)-4-{(1S)-1-carboxyethoxy}-3-benzamido-1-(1-diphenylmethoxycarbonyl-1-triphenylphosphoranylidenemethyl)azetidin-2-one 2.50 Grams of the product of the step (3) above was dissolved in 37 ml of acetone, to which were then added 12 ml of water and 3.16 ml of aqueous 1N NaOH solution. The mixture was agitated at room temperature for 2 hours, followed by further addition of 1.6 ml of aqueous 1N NaOH solution and agitation at room temperature for 30 minutes.

The resultant reaction solution was adjusted to pH 7.0 and concentrated, and the residue was triturated with isopropyl ether and filtered to give a powder.

The powder was then suspended in a mixture of 50 ml of water and 50 ml of ethyl acetate. The suspension was adjusted to pH 2.0 with ice-cooling and the organic layer was separated, dried over MgSO$_4$ and concentrated to yield 2.28 g (95%) of the title compound having the structure:

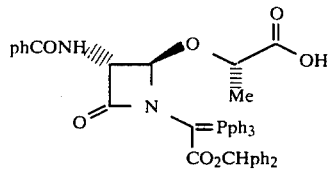

IR (CHCl$_3$), $\nu_{max}$ (cm$^{-1}$): 1765, 1730, 1658, 1617.

(5) Preparation of (3R,4R)-4-{(1S)-3-(1-methyl-1H-tetrazole-5-yl)thio-2-oxo-1-methylpropoxy}-3-benzamido-1-(1-diphenylmethoxycarbonyl-1-triphenylphosphoranylidenemethyl)azetidin-2-one 2.10 Grams of the product of the step (4) was dissolved in 25 ml of methylene chloride, to which were added at −10° C. 0.36 ml of N-methylmorpholine and 0.29 ml of ethyl chloroformate. The mixture was agitated at that temperature for 30 minutes.

To the reaction solution so obtained was added dropwise with ice-cooling 10 ml of ethyl ether containing 5.5 mmole of diazomethane. After completion of the addition, the mixture was agitated for 30 minutes to give a solution comprising (3R,4R)-4-{(1S)-3-diazo-2-oxo-1-methylpropoxy}-3-benzamido-1-(1-diphenylmethoxycarbonyl-1-triphenylphosphoranylidenemethyl)azetidin-2-one.

0.91 ml of a solution of 6N HCl in dioxane was added dropwise with ice-cooling to the solution obtained just above, and the mixture was stirred at that temperature for 30 minutes. The resultant reaction solution was poured into 10 ml of ice water. The organic layer was separated, washed with saturated aqueous sodium bicarbonate and with water, dried over MgSO$_4$ and concentrated to give 2.05 g of an oil product of (3R,4R)-4-{(1S)-3-chloro-2-oxo-1-methylpropoxy}-3-benzamido-1-(1-diphenylmethoxycarbonyl-1-triphenylphosphoranylidenemethyl)azetidin-2-one.

The oil product was taken up in 20 ml of methylene chloride, to which were then added 0.32 g of 1-methyl-5-mercapto-1H-tetrazole and 0.26 ml of pyridine, followed by agitation at room temperature for 15 hours. The reaction solution was poured into 20 ml of ice water.

The organic layer was separated, washed with saturated aqueous sodium bicarbonate and with water, dried over MgSO$_4$ and concentrated.

The residue was purified by a column chromatography on silica gel developed with benzene-ethyl acetate (2:1) to afford 1.70 g (72%) of the title compound, that is, (3R,4R)-4-{(1S)-3-(1-methyl-1H-tetrazole-5-yl)thio-2-oxo-1-methylpropoxy}-3-benzamido-1-(1-diphenylmethoxycarbonyl-1-triphenylphosphoranylidenemethyl)azetidin-2-one.

IR (CHCl$_3$), $\nu_{max}$ (cm$^{-1}$): 1765, 1735, 1658, 1619

EXAMPLE 18

(1) Preparation of (3R,4R)-4-{(1R)-3-diazo-2-oxo-1-methylpropoxy}-3-benzamido-1-(1-diphenylmethoxycarbonyl-1-triphenylphosphoranylidenemethyl)azetidin-2-one 3.29 Grams of the product obtained in the step (5) of Example 9 was dissolved in 40 ml of methylene chloride, to which were added at −10° C. 0.57 ml of N-methylmorpholine and 0.45 ml of ethyl chloroformate. The mixture was stirred at −10° C. for 30 minutes.

To the reaction solution was added dropwise under ice-cooling 10 ml of ethyl ether containing 8 mmole of diazomethane. After completion of the addition, the mixture was agitated for 30 minutes, followed by addition of 0.23 ml of acetic acid and further stirring for 30 minutes.

The resultant reaction solution was poured into ice water, and the organic layer was separated, washed with saturated aqueous sodium bicarbonate and then with water, dried over MgSO$_4$ and then concentrated.

The residue was purified by a column chromatography on silica gel developed with a solvent of benzene-ethyl acetate (3:1) to afford 2.91 g (86%) of the title compound having the structure:

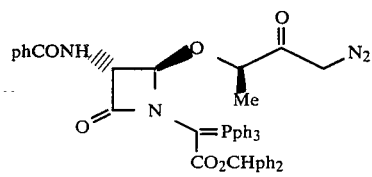

IR (CHCl$_3$), $\nu_{max}$ (cm$^{-1}$): 2110, 1763, 1665, 1618

(2) Preparation of (3R,4R)-4-{(1R)-3-chloro-2-oxo-1-methylpropoxy}-3-benzamido-1-(1-diphenylmethoxycarbonyl-1-triphenylphosphoranylidenemethyl)azetidin-2-one The product (2.91 g) of the step (1) above was dissolved in 40 ml of methylene chloride, to which was then added 0.92 ml of a solution of 6N HCl in dioxane dropwise with ice-cooling. The mixture was stirred at that temperature for 30 minutes. The resultant reaction solution was poured into 50 ml of ice water.

The organic layer was separated, washed with saturated aqueous sodium bicarbonate and then with water, dried over MgSO$_4$ and concentrated to give 2.73 g (93%) of the title compound of the structure:

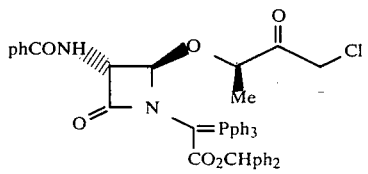

IR (CHCl$_3$), $\nu_{max}$ (cm$^{-1}$): 1765, 1742, 1650, 1618.

(3) Preparation of (3R,4R)-4-{(1R)-3-(2-methyl-1,3,4-thiadiazole-5-yl)thio-2-oxo-1-methylpropoxy}-3-benzamido-1-(1-diphenylmethoxycarbonyl-1-triphenylphosphoranylidenemethyl)azetidin-2-one The product (1.76 g) obtained in the step (2) above was dissolved in 30 ml of methylene chloride, to which were added 0.35 g of 2-methyl-5-mercapto-1,3,4-thiadiazole and 0.26 ml of pyridine. The mixture was agitated at room temperature for 15 hours and then poured into 30 ml of ice water.

The organic layer was separated, washed with saturated aqueous sodium bicarbonate and with water, dried over MgSO$_4$ and concentrated.

The residue was purified by a column chromatography on silica gel developed with benzene-ethyl acetate (2:1) to afford 1.40 g (71%) of the title compound.

IR (CHCl$_3$), $\nu_{max}$ (cm$^{-1}$): 1763, 1737, 1652, 1615.

EXAMPLE 19

(1) Preparation of (3R,4R)-4-{(1S)-1-carboxyethoxy}-3-benzamido-1-(1-diphenylmethoxycarbonyl-2-methylprop-1-enyl)azetidin-2-one 6.10 g of the compound (A) indicated in step (1) of Example 9 was dissolved in 70 ml of acetone, and to the solution was added under ice-cooling 30 ml of water containing 470 mg of sodium hydroxide. The mixture was stirred at that temperature for one hour and then at room temperature for further one hour, and the acetone was distilled off.

The resultant aqueous solution was washed with ethyl ether, adjusted to an acidic pH value of 2.0 and extracted with ethyl acetate.

The organic extract was dried over MgSO$_4$ and concentrated, followed by crystallization from ethyl ether to give 5.30 g (91%) of the title compound.

m.p. 172°–174° C. (decomp.)

IR (CHCl$_3$), $\nu_{max}$ (cm$^{-1}$): 1775, 1724, 1660, 1605

NMR (CDCl$_3$), $\delta_{ppm}$: 1.40 (3H, d, J=6.8 Hz, —CHCH$_3$), 2.01 (3H, s, =⟨ CH$_3$), 2.23 (3H, s, =⟨ CH$_3$), 4.41 (1H, q, J=6.8 Hz, —CHCH$_3$), 4.75 (1H, dd, J=6, 1 Hz, 3-H), 5.14 (1H, s, 4-H), 6.82 (1H, s, —CHph$_2$), 6.90–7.80 (15H, m, C$_6$H$_5$ x3).

(2) Preparation of (3R,4R)-4-{(1S)-3-diazo-2-oxo-1-methylpropoxy}-3-benzamido-1-(1-diphenylmethoxycarbonyl-2-methylprop-1-enyl)azetidin-2-one 5.00 Grams of the product of the step (1) above was dissolved in 70 ml of methylene chloride, to which were added at −10° C. 1.19 ml of N-methylmorpholine and 0.96 ml of ethyl chloroformate. The mixture was agitated at −10° C. for 30 minutes.

To the reaction solution was added dropwise with ice-cooling 40 ml of ethyl ether containing 18 mmole of diazomethane. After completion of the addition, the mixture was agitated for 30 minutes, followed by addition of 0.57 ml of acetic acid and further stirring for 10 minutes. The resultant reaction solution was poured into 100 ml of ice water.

The organic layer was separated, washed with saturated aqueous sodium bicarbonate and with water, and concentrated. There was thus obtained 5.15 g of the title compound of the structure:

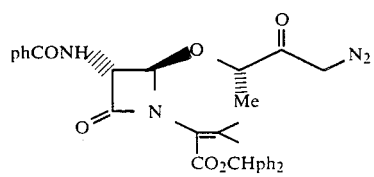

IR (CCl₄), $\nu_{max}$ (cm⁻¹): 2210, 1775, 1722, 1660.

NMR (CDCl₃), $\delta_{ppm}$: 1.32 (3H, d, J=6.8 Hz, —CHCH₃), 2.07 (3H, s, CH₃), 2.28 (3H, s, CH₃), 4.15 (1H, q, J=6.8 Hz, —CHCH₃), 4.83 (1H, dd, J=7, 1 Hz, 3-H), 5.04 (1H, d, J=1 Hz, 4-H), 5.30 (1H, s, —CHN₂), 6.88 (1H, s, —CHph₂), 7.10–7.85 (15H, m, C₆H₅ x3).

(3) Preparation of (3R,4R)-4-{(1S)-3-chloro-2-oxo-1-methylpropoxy}-3-benzamido-1-(1-diphenylmethoxycarbonyl-2-methylprop-1-enyl)azetidin-2-one The product (5.15 g) of the step (2) above was dissolved in 50 ml of methylene chloride, to which was added dropwise under ice-cooling 9 ml of a solution of 1N HCl in dioxane. The mixture was stirred at that temperature for 30 minutes and then poured into 50 ml of ice water.

The organic layer was separated, washed with saturated aqueous sodium bicarbonate and with water, dried over MgSO₄ and concentrated to give 5.10 g of the title compound having the structure:

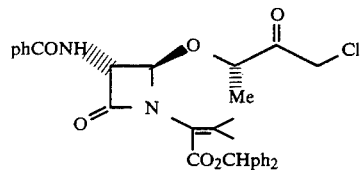

IR (CHCl₃), $\nu_{max}$ (cm⁻¹): 1772, 1723, 1663, 1603

NMR (CDCl₃), $\delta_{ppm}$: 1.34 (3H, d, J=6.8 Hz, —CHCH₃), 2.04 (3H, s, CH₃), 2.27 (3H, s, CH₃), 4.05 (2H, s, —CH₂Cl), 4.27 (1H, q, J=6.8 Hz, —CHCH₃), 4.78 (1H, dd, J=7 Hz, 3-H), 5.06 (1H, d, J=1 Hz, 4-H), 6.88 (1H, s, —CHph₂), 7.00–7.90 (15H, m, C₆H₅ x3).

(4) Preparation of (3R,4R)-4-{(1S)-3-(1-methyl-1H-tetrazole-5-yl)thio-2-oxo-1-methylpropoxy}-3-benzamido-1-(1-diphenylmethoxycarbonyl-1-triphenylphosphoranylidenemethyl)azetidin-2-one The product (5.10 g) obtained in the step (3) above was dissolved in 50 ml of methylene chloride, to which were added 1.06 g of 1-methyl-5-mercapto-1H-tetrazole and 0.9 ml of pyridine. The mixture was agitated at room temperature for 15 hours and then poured into 50 ml of ice water.

The organic layer was separated, washed with saturated aqueous sodium bicarbonate and with water, dried over MgSO₄ and concentrated.

The residue was purified by a column chromatography on silica gel developed with benzene-ethyl acetate (3:1) to afford 5.16 g (89%) of the title compound having the structure:

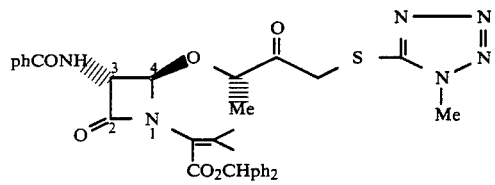

IR (CHCl₃), $\nu_{max}$ (cm⁻¹): 1773, 1725, 1665, 1605.

NMR (CDCl₃), $\delta_{ppm}$: 1.35 (3H, d, J=6.8 Hz, —CHCH₃), 2.20 (3H, s, CH₃), 2.28 (3H, s, CH₃), 3.86 (3H, s, tetrazole 1-CH₃), 4.22 (2H, s, —CH₂S—), 4.37 (1H, q, J=6.8 Hz, —CHCH₃), 4.83 (1H, dd, J=6, 1 Hz, 3-H), 5.21 (1H, d, J=1 Hz, 4-H), 6.86 (1H, s, —CHph₂), 7.00–7.80 (15H, m, C₆H₅ x3).

(5) Preparation of (3R,4R)-4-{(1S)-3-(1-methyl-1H-tetrazole-5-yl)thio-2-oxo-1-methylpropoxy}-3-benzamido-1-(1-diphenylmethoxycarbonyl-1-hydroxymethyl)azetidin-2-one 2.00 Grams of (3R,4R)-4-{(1R)-3-(1-methyl-1H-tetrazole-5-yl)thio-2-oxo-1-methylpropoxy}-3-benzamido-1-(1-diphenylmethoxycarbonyl-2-methylprop-1-enyl)azetidin-2-one was dissolved in 80 ml of methylene chloride and ozone was passed into the solution at −60° C. until the latter turned blue.

To the resultant solution were added at −60° C. 0.40 g of zinc powder and 0.4 ml of acetic acid and the temperature of the mixture was raised to 0° C., followed by further addition of 3.98 g of zinc powder and 3.60 ml of acetic acid at that temperature. The mixture was agitated for 30 minutes.

The reaction mixture thus obtained was filtered and the filtrate was washed with saturated aqueous sodium bicarbonate and with water, dried over MgSO₄ and concentrated to give 1.10 g (57%) of the title compound having the structure:

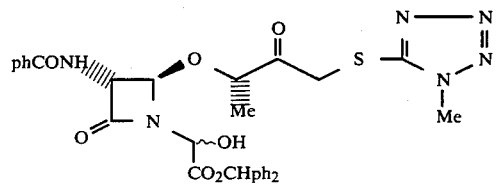

IR (CHCl₃), $\nu_{max}$ (cm⁻¹): 3400, 1776, 1740, 1664, 1604.

(6) Preparation of (3R,4R)-4-{(1S)-3-(1-methyl-1H-tetrazole-5-yl)thio-2-oxo-1-methylpropoxy}-3-benzamido-1-(1-diphenylmethoxycarbonyl-1-chloromethyl)azetidin-2-one The product (1.38 g) of the step (5) above was dissolved in 40 ml of methylene chloride, and to the solution after ice-cooling were added 0.53 ml of pyridine and 0.48 ml of thionyl chloride, followed by agitation for 15 minutes. The reaction solution was poured into 50 ml of ice water.

The organic layer was separated, washed with saturated aqueous sodium carbonate and with water, dried over MgSO₄ and concentrated. There was thus obtained 1.21 g (63%) of the title compound having the structure:

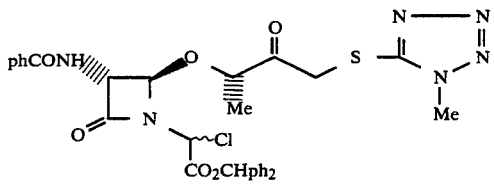

IR (CHCl₃), $\nu_{max}$ (cm⁻¹): 1789, 1752, 1663, 1603.

(7) Preparation of (3R,4R)-4-{(1S)-3-(1-methyl-1H-tetrazole-5-yl)thio-2-oxo-1-methylpropoxy}-3-benzamido-1-(1-diphenylmethoxycarbonyl-1-triphenylphosphoranylidenemethyl-)azetidin-2-one The product (1.20 g) of the step (6) above was dissolved in 40 ml of chloroform, to which was then added 0.57 g of triphenylphosphine, and the mixture was stirred at ambient temperature for 15 hours. The reaction solution so obtained was washed with saturated aqueous sodium bicarbonate and with water, dried over MgSO$_4$ and then concentrated.

The residue was purified by a column chromatography on silica gel developed with benzene-ethyl acetate (2:1) to give 0.86 g (53%) of the title compound.

IR (CHCl$_3$), $\nu_{max}$ (cm$^{-1}$): 1765, 1735, 1658, 1619.

EXAMPLE 20

(1) Preparation of (3R,4R)-4-{(1S)-3-iodo-2-oxo-1-methylpropoxy}-3-benzamido-1-(1-diphenylmethoxycarbonyl-2-methylprop-1-enyl)azetidin-2-one The product (1.32 g) obtained in the step (3) of Example 18 was dissolved in 30 ml of acetone, and 0.9 g of sodium iodide was added to the solution. The mixture was agitated at room temperature for 20 minutes and then concentrated.

The residue was taken up in 20 ml of ethyl acetate, and the solution was washed with aqueous sodium thiosulfate and with water, dried over MgSO$_4$ and concentrated to yield 1.32 g (86%) of the title compound of the structure:

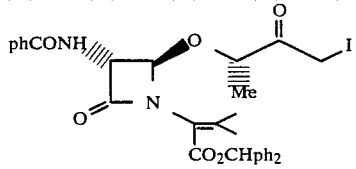

NMR (CDCl$_3$), $\delta_{ppm}$: 1.40 (3H, d, J=6.8 Hz, —CHCH$_3$), 2.07 (3H, s, CH$_3$), 2.30 (3H, s, CH$_3$), 3.56, 3.76 (2H, ABq, J=10 Hz, —CH$_2$I), 4.44 (1H, q, J=6.8 Hz, —CHCH$_3$), 4.83 (1H, dd, J=7, 1 Hz, 3-H), 5.08 (1H, d, J=1 Hz, 4-H), 6.90 (1H, s, —CHph$_2$), 7.00–7.90 (15H, m, C$_6$H$_5$ x3).

(2) Preparation of (3R,4R)-4-{(1S)-2-oxo-1-methylpropoxy}-3-benzamido-1-(1-diphenylmethoxycarbonyl-2-methylprop-1-enyl)azetidin-2-one The product (1.32 g) of the step (1) above was dissolved in 15 ml of methylene chloride, and the solution was admixed under ice-cooling with 3.12 g of zinc powder and 2.9 ml of acetic acid. The admixture was stirred at that temperature for 30 minutes. The reaction mixture thus obtained was filtered and the filtrate was washed with saturated aqueous sodium bicarbonate and with water, dried over MgSO$_4$ and concentrated.

The residue was purified by a column chromatography on silica gel developed with benzene-ethyl acetate (4:1) to afford 0.75 g (70%) of the title compound having the structure:

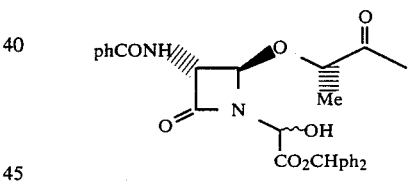

IR (CHCl$_3$), $\nu_{max}$ (cm$^{-1}$): 1771, 1723, 1665, 1604.
NMR (CDCl$_3$), $\delta_{ppm}$: 1.28 (3H, d, J=7 Hz, —CHCH$_3$), 1.90 (3H, s, —COCH$_3$), 2.03 (3H, s, =CH$_3$), 2.25 (3H, s, =CH$_3$), 4.17 (1H, q, J=7 Hz, —CHCH$_3$), 4.79 (1H, dd, J=7, 1 Hz, 3-H), 5.01 (1H, d, J=1 Hz, 4-H), 6.87 (1H, s, —CHph$_2$), 7.00–7.80 (15H, m, C$_6$H$_5$ x3).

(3) Preparation of (3R,4R)-4-{(1S)-2-oxo-1-methylpropoxy}-3-benzamido-1-(1-diphenylmethoxycarbonyl-1-hydroxymethyl)azetidin-2-one The product (210 mg) obtained in the step (2) above was dissolved in 15 ml of methylene chloride, and ozone was passed into the solution at −60° C. until the latter turned blue. To the reaction solution were added at −60° C. 50 mg of zinc powder and 0.05 ml of acetic acid, and the temperature of the mixture was raised to 0° C., followed by further addition of 510 mg of zinc powder and 0.05 ml of acetic acid. The resultant mixture was agitated at that temperature for 30 minutes and then filtered. The filtrate was washed with saturated aqueous sodium bicarbonate and with water, dried over MgSO$_4$ and concentrated.

The residue was purified by a column chromatography on silica gel to give 115 mg (57%) of the title compound having the structure:

IR (CHCl$_3$), $\nu_{max}$ (cm$^{-1}$): 3450, 1780, 1745, 1724, 1663.
NMR (CDCl$_3$), $\delta_{ppm}$: 1.17, 1.38 (3H, d, —CHCH$_3$), 2.00, 2.04 (3H, s, —COCH$_3$), 4.30, 4.45 (1H, q, —CHCH$_3$), 4.67, 4.70 (1H, dd, 3-H), 4.76, 4.94 (1H, d, 4-H), 5.30, 5.40 (1H, br.s, —CHOH), 6.88, 6.90 (1H, s, —CHph$_2$), 7.00–7.80 (15H, m, C$_6$H$_5$ x3).

(4) Preparation of (3R,4R)-4-{(1S)-2-oxo-1-methylpropoxy}-3-benzamido-1-(1-diphenylmethoxycarbonyl-1-chloromethyl)azetidin-2-one 115 mg of the product from the step (3) above was dissolved in 2 ml of methylene chloride, and to the solution after ice-cooling were added 32 μl of pyridine and 32 μl of thionyl chloride, followed by agitation at that temperature for 30 minutes. The reaction solution was poured into ice water.

The organic layer was separated, washed with saturated aqueous sodium carbonate and with water, dried over MgSO$_4$ and concentrated. There was thus obtained 109 g (92%) of the title compound.

NMR (CDCl$_3$), δ$_{ppm}$: 1.26, 1.28 (3H, d, —CHCH$_3$), 1.96 (3H, s, ≕CH$_3$), 2.08 (3H, s, ≕CH$_3$), 4.22, 4.25 (1H, q, —CHCH$_3$), 4.67, 4.72 (1H, dd, 3-H), 5.31, 5.47 (1H, d, 4-H), 6.25 (1H, s, —CHC), 6.83, 6.87 (1H, s, —CHph$_2$), 7.00–7.80 (15H, m, C$_6$H$_5$ x3).

(5) Preparation of (3R,4R)-4-{(1S)-2-oxo-1-methylpropoxy}-3-benzamido-1-(1-diphenylmethoxycarbonyl-1-triphenylphosphoranylidenemethyl)azetidin-2-one 195 mg of the product from the step (4) above was dissolved in 50 ml of chloroform, to which were then added 44 mg of triethylamine and 190 mg of triphenylphosphine, and the mixture was stirred at ambient temperature for 15 hours.

The reaction solution was poured into ice water and the organic layer was separated, washed with saturated aqueous sodium bicarbonate and with water, dried over MgSO$_4$ and then concentrated.

The residue was purified by a column chromatography on silica gel to yield 144 mg (53%) of the title compound.

IR (CHCl$_3$), ν$_{max}$ (cm$^{-1}$): 1763, 1720, 1660, 1625.

EXAMPLE 21

(1) Preparation of (3R,4R)-4-{(1R)-1-ethoxycarbonylethoxy}-3-benzamido-1-(1-diphenylmethoxycarbonyl-2-methylprop-1-enyl)-azetidin-2-one 10 Grams of (1R,5S)-3-phenyl-6-(1-diphenylmethoxycarbonyl-2-methylprop-1-enyl)-7-oxo-4-oxa-2,6-diazabicyclo[3,2,0]hept-2-ene as used in Example 9(1) was dissolved in 35 ml of L-(+)-lactic acid ethyl ester instead of the DL-α-lactic acid ethyl ester employed in Reference Example 1(1). To the resultant solution was added 0.5 ml of trifluoromethanesulfonic acid, and the mixture was stirred at ambient temperature for 1.5 hours. The reaction solution thus obtained was poured into 200 ml of aqueous sodium bicarbonate and allowed to stand under ice-cooling for 30 minutes.

The aqueous layer was removed to leave an oil product, which was then taken up in 70 ml of ethyl acetate, washed with saturated aqueous sodium chloride and with water, dried over MgSO$_4$ and concentrated.

The residue was purified by a column chromatography on silica gel developed with benzene-ethyl acetate (7:1), followed by crystallization from ethyl ether. There was thus afforded 4.3 g (34%) of the title compound, namely the compound (A) as indicated in Example 9(1). This product was obtained in a higher yield than in Example 9(1).

What is claimed is:

1. A compound of the formula:

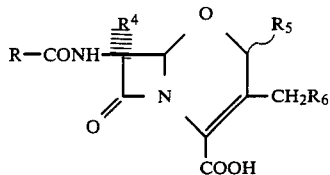

(I)

and a pharmaceutically acceptable salt or ester thereof, wherein R represents a group of the formula:

in which R$_1$ is a 2-thienyl or 3-thienyl group, and R$_2$ is a hydrogen atom or a carboxyl group, or R-represents a group of the formula:

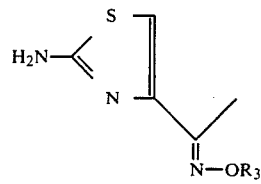

in which R$_3$ is a hydrogen atom, a lower alkyl or carboxyllower alkyl group; R$_4$ represents a hydrogen atom or a methoxy group, R$_5$ represents a lower alkyl group; R$_6$ represents hydrogen, azido, halo, cyano, hydroxy, carbamoyloxy, N-loweralkyl carbamoyloxy, N,N-diloweralkyl carbamoyloxy, amino, mercapto, loweralkylthio, loweralkanoyloxy, benzoyloxy, or a 5- or 6-membered optionally substituted heterocyclic thio radical selected from the group consisting of tetrazol-5-ylthio; 1-methyltetrazol-5-ylthio; 1-carboxymethyltetrazol-5-ylthio; 1-sulfomethyltetrazol-5-ylthio; N,N-dimethylaminoethyltetrazol-5-ylthio; 1,3,4-thiadiazol-5-ylthio; 2-methyl-1,3,4-thiadiazol-5-ylthio; 2-carboxymethyl-3-methyl-thiazol-5-ylthio; 1,2,3-triazol-5-ylthio; 4-carboxy-3-hydroxy-1,2-oxazol-5-ylthio; 6-hydroxy-2-methyl-1,2,4-triazin-5-on-3-ylthio.

2. A compound according to claim 1 wherein R$_6$ is selected from the group consisting of tetrazol-5-ylthio; 1-methyltetrazol-5-ylthio; 1-carboxymethyltetrazol-5-ylthio; 1-sulfomethyltetrazol-5-ylthio; N,N-dimethylaminoethyltetrazol-5-ylthio; 1,3,4-thiadiazol-5-ylthio; 2-methyl-1,3,4-thiadiazol-5-ylthio; 2-carboxymethyl-3-methylthiazol-5-ylthio; 1,2,3-triazol-5-ylthio; 4-carboxy-3-hydroxy-1,2-oxazol-5-ylthio; 6-hydroxy-2-methyl-1,2,4-triazin-5-on-3-ylthio.

3. A compound of the formula:

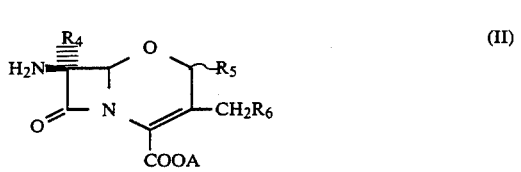

(II)

wherein R$_4$ represents a hydrogen atom or a methoxy group, R$_5$ represents a lower alkyl group, R$_6$ represents hydrogen, azido, halo, cyano, hydroxy, carbamoyloxy, N-loweralkyl carbamoyloxy, N,N-di-loweralkyl carbamoyloxy, amino, mercapto, loweralkylthio, loweralkanoyloxy, aroyloxy, or a 5- or 6-membered optionally substituted heterocyclic thio radical, and A represents a hydrogen atom or a carboxyl-protecting group selected from phenyl methyl, diphenyl methyl, benzyl, p-nitrobenzyl, t-butyl and trichloroethyl.

4. A process for the production of a compound of the formula:

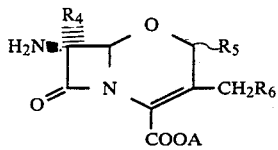

(II)

wherein R4 represents a hydrogen atom or a methoxy group, R5 represents a lower alkyl group, R6 represents hydrogen, azido, halo, cyano, hydroxy, carbamoyloxy, N-loweralkyl carbamoyloxy, N,N-di-loweralkyl carbamoyloxy, amino mercapto, loweralkylthio, loweralkanoyloxy, aroyloxy, or a 5- or 6-membered optionally substituted heterocyclic thio radical, and A represents a hydrogen atom or a carboxyl-protecting group, selected from phenyl methyl, diphenyl methyl benzyl, p-nitrobenzyl, t-butyl and trichloroethyl, characterized in that the process comprises cyclizing a compound of the formula:

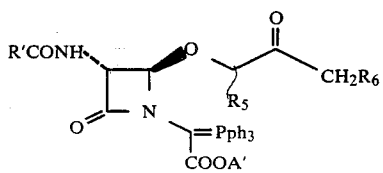

(III)

wherein the group R'CO— represents an acyl group, selected from phenylcarbonyl, phenylacetyl, benzoyloxycarbonyl, phenoxymethylcarbonyl, or tritylcarbonyl, R5 and R6 are as defined above, ph represents a phenyl group, and A' represents a carboxyl-protecting group, to produce a compound of the formula:

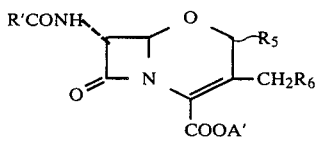

(IV)

wherein R'CO—, R5, R6, and A' are as defined above; removing the group R'CO— from the 7α-amino group of the compound (IV) in a known manner to produce a compound of the formula:

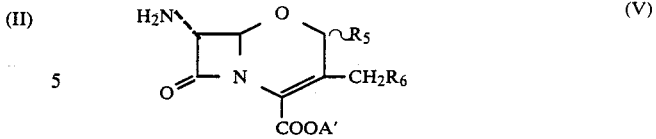

(V)

in which R5, R6 and A' are as defined above; reacting the compound (V) with an aromatic aldehyde of the formula R"CHO to produce a compound in the form of a Schiff base-type compound of the formula:

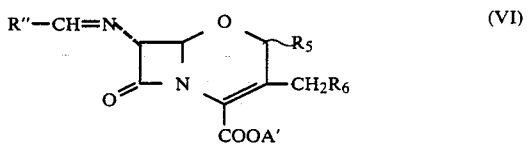

(VI)

wherein R5, R6 and A' are as defined above, and R" represents an aromatic group selected from phenyl, hydroxyphenyl, and loweralkyl substituted phenyl or hydroxyphenyl; subjecting the Schiff base-modified 7α-amino group of the compound (VI) to either a known reaction for steric inversion, comprising first treating the compound with an oxidizing agent selected from manganese dioxide, nickel peroxide, lead tetraacetate and dichlorodicyanobenzoquinone, removal of the oxidizing agent, followed by treatment with a reducing agent selected from sodium cyanoborohydride, sodium borohydride, tetraethylammonium borohydride and tri-t-butoxy lithium aluminum hydride, or a known reaction for steric inversion accompanied by β-methoxylation at the 7-position of the compound comprising contacting the said Schiff base modified amino group with nickel peroxide followed by methanol (VI), thereby producing a compound of the formula:

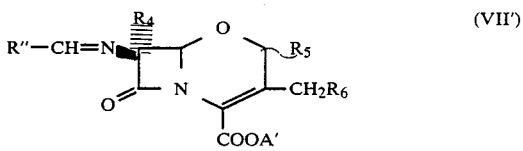

(VII')

wherein R4 represents a hydrogen atom or a methoxy group and R5, R6, R" and A' are as defined above; cleaving the Schiff base moiety R"—CH= from the compound (VII') in a conventional manner; and removing, if necessary, the carboxyl-protecting group (A') from the resultant product compound.

* * * * *